US011884966B2

(12) United States Patent
Lo et al.

(10) Patent No.: US 11,884,966 B2
(45) Date of Patent: Jan. 30, 2024

(54) TISSUE-SPECIFIC METHYLATION MARKER

(71) Applicant: GRAIL, LLC, Menlo Park, CA (US)

(72) Inventors: Yuk-Ming Dennis Lo, Hong Kong (CN); Rossa Wai Kwun Chiu, Hong Kong (CN); Kwan Chee Chan, Hong Kong (CN); Wanxia Gai, Hong Kong (CN); Lu Ji, Hong Kong (CN)

(73) Assignee: GRAIL, LLC, Menlo Park, CA (US)

(*) Notice: Subject to any disclaimer, the term of this patent is extended or adjusted under 35 U.S.C. 154(b) by 260 days.

(21) Appl. No.: 16/354,799

(22) Filed: Mar. 15, 2019

(65) Prior Publication Data

US 2019/0390257 A1 Dec. 26, 2019

Related U.S. Application Data

(60) Provisional application No. 62/769,928, filed on Nov. 20, 2018, provisional application No. 62/643,649, filed on Mar. 15, 2018.

(51) Int. Cl.
*C12Q 1/68* (2018.01)
*C12Q 1/6823* (2018.01)
*C12Q 1/6886* (2018.01)

(52) U.S. Cl.
CPC ......... *C12Q 1/6823* (2013.01); *C12Q 1/6886* (2013.01); *C12Q 2600/112* (2013.01); *C12Q 2600/118* (2013.01); *C12Q 2600/154* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 8,741,811 B2 | 6/2014 | Lo et al. | |
| 2014/0080715 A1* | 3/2014 | Lo | C12Q 1/6881 506/2 |
| 2015/0322513 A1 | 11/2015 | Gromminger et al. | |
| 2016/0017419 A1* | 1/2016 | Chiu | G16B 30/10 506/2 |
| 2016/0194721 A1* | 7/2016 | Allawi | C12Q 1/6881 435/6.11 |
| 2016/0340740 A1 | 11/2016 | Zhang | |
| 2017/0121767 A1* | 5/2017 | Dor | C12Q 1/6886 |
| 2017/0191135 A1 | 7/2017 | Pedersen et al. | |
| 2017/0314073 A1 | 11/2017 | Grömminger et al. | |

FOREIGN PATENT DOCUMENTS

| | | | |
|---|---|---|---|
| WO | WO-2014043763 A1 | 3/2014 | |
| WO | WO 2017/129716 A1 | 8/2017 | |
| WO | WO-2017212428 A1 | 12/2017 | |
| WO | WO-2019178496 A1 | 9/2019 | |

OTHER PUBLICATIONS

Barault (Annals of Oncology 26, 1994-1999, 2015) (International Journal of Molecular Sciences 2016 17, 484, pp. 1-9).*
Vietsch (Cancer Genetics 218-219 (2017) pp. 39-50).*
Guan (Acta Pharmaceutica Sinica B 2015, 5(5):402-418).*
de Vos et al., 2017, Comparison of quantification algorithms for circulating cell free DNA methylation biomarkers in blood plasma from cancer patients, Clinical Epigentics, 9:125, 1-11 (Year: 2017).*
Danese et al., 2013, Epigenetic alteration: new insights moving from tissue to plasma—the example of PCDH10 promoter methylation in colorectal cancer, British Journal of Cancer, 109, 807-813 (Year: 2013).*
Altschul, et al. Gapped BLAST and PSI-BLAST: a new generation of protein database search programs. Nucleic Acids Res. Sep. 1, 1997;25(17):3389-402.
Cai, X.et al. Accessing genetic information with liquid biopsies. Trends Genet 2015;31:564-75.
Chan, et al. Analysis of plasma epstein-barr virus DNA to screen for nasopharyngeal cancer. N Engl J Med 2017;377:513-22.
Chan, KCA, et al. Ambient temperature and screening for nasopharyngeal cancer. N Engl J Med 2018;378:962-3.
Chan, KCA et al. Cancer genome scanning in plasma: Detection of tumor-associated copy number aberrations, single-nucleotide variants, and tumoral heterogeneity by massively parallel sequencing. Clin Chem 2013;59:211-24.
Chan, KCA, et al. Early detection of nasopharyngeal carcinoma by plasma epstein-barr virus DNA analysis in a surveillance program. Cancer 2013;119:1838-44.
Chan, K.C.A. et al. Effects of preanalytical factors on the molecular size of cell-free DNA in blood. Clin Chem 2005;51:781-4.
Chan, KCA, et al. Noninvasive detection of cancer-associated genomewide hypomethylation and copy number aberrations by plasma DNA bisulfite sequencing. Proc Natl Acad Sci U S A 2013;110:18761-8.
Chan, KCA, et al. Persistent aberrations in circulating DNA integrity after radiotherapy are associated with poor prognosis in nasopharyngeal carcinoma patients. Clin Cancer Res 2008;14:4141-5.
Chim, S.S.C. et al. Detection of the placental epigenetic signature of the maspin gene in maternal plasma. Proc Natl Acad Sci USA 102(41):14753-14758 (Oct. 11, 2005).
Chiu, R.W.K. et al. Effects of blood-processing protocols on fetal and total DNA quantification in maternal plasma. Clin Chem 2001;47:1607-13.

(Continued)

*Primary Examiner* — Jehanne S Sitton
(74) *Attorney, Agent, or Firm* — Greenberg Traurig, LLP

(57) ABSTRACT

Provided herein are compositions comprising tissue-specific markers for identifying a tissue of origin of a cell-free nucleic acid, e.g., a cell-free DNA molecule. Also provided herein are methods, compositions, and systems for identifying a tissue of origin of a cell-free nucleic acid by determining an absolute amount of cell-free nucleic acids comprising the tissue-specific marker. Also provided herein are methods, compositions, and systems for detecting a cancer in a tissue of an organism by analyzing tissue-specific markers.

20 Claims, 12 Drawing Sheets

Specification includes a Sequence Listing.

(56) References Cited

OTHER PUBLICATIONS

Dressman et al. Transforming single DNA molecules into fluorescent magnetic particles for detection and enumeration of genetic variations. Proc. Natl. Acad. Sci. 2003. 100(15):8817-8822.

Gai et al. Liver- and colon-specific DNA methylation markers in plasma for investigation of colorectal cancers with or without liver metastases; Clinical Chemistry, vol. 64, No. 8, pp. 1239-1249 (2018).

Goldman, JW et al. Are liquid biopsies a surrogate for tissue egfr testing? Ann Oncol 2018;29:i38-i46.

Guo, S. et al. Identification of methylation haplotype blocks aids in deconvolution of heterogeneous tissue samples and tumor tissue-of-origin mapping from plasma DNA. Nat Genet 2017;49:635-42.

Jiang, P. et al. Lengthening and shortening of plasma DNA in hepatocellular carcinoma patients. Proc Natl Acad Sci U S A 2015;112:E1317-25.

Karlin, et al. Applications and statistics for multiple high-scoring segments in molecular sequences. Proc Natl Acad Sci U S A. Jun. 15, 1993;90(12):5873-7.

Lam, W.K.J. et al. DNA of erythroid origin is present in human plasma and informs the types of anemia. Clin Chem 2017;63:1614-23.

Leary, et al. Detection of chromosomal alterations in the circulation of cancer patients with whole-genome sequencing. Sci Transl Med. Nov. 28, 2012;4(162):162ra154 . . .

Leary, et al. Development of personalized tumor biomarkers using massively parallel sequencing. Sci Transl Med. Feb. 24, 2010;2(20):20ra14 . . .

Lehmann-Werman, R. et al. Identification of tissue-specific cell death using methylation patterns of circulating DNA. Proc Natl Acad Sci U S A 2016;113:E1826-34.

Li, R. et al. Soap2: An improved ultrafast tool for short read alignment. Bioinformatics 2009;25:1966-7.

Lo, Y.M. Dennis, et al. Maternal Plasma DNA Sequencing Reveals the Genome-Wide Genetic and Mutational Profile of the Fetus. Sci. Transl. Med. 2(61):61ra91:1-14 (Dec. 8, 2010).

Lo, Y.M.D. Digital pcr for the molecular detection of fetal chromosomal aneuploidy. Proc Natl Acad Sci U S A 2007;104:13116-21.

Martens, J.H., Stunnenberg HG. Blueprint: Mapping human blood cell epigenomes. Haematologica 2013;98:1487-9.

Mayo-de-Las-Casas C. et al. Large scale, prospective screening of egfr mutations in the blood of advanced nsclc patients to guide treatment decisions. Ann Oncol 2017;28:2248-55.

PCT/US19/22504 Search Report & Written Opinion dated Aug. 16, 2019.

Roadmap Epigenomics C, et al. Integrative analysis of 111 reference human epigenomes. Nature 2015;518:317-30.

Schrock, A. et al. Free-circulating methylated DNA in blood for diagnosis, staging, prognosis, and monitoring of head and neck squamous cell carcinoma patients: An observational prospective cohort study. Clin Chem 2017;63:1288-96.

Snyder, M.W. et al. Cell-free DNA comprises an in vivo nucleosome footprint that informs its tissues-of-origin. Cell 2016;164:57-68.

Sun, K. et al. Plasma DNA tissue mapping by genome-wide methylation sequencing for noninvasive prenatal, cancer, and transplantation assessments. Proc Natl Acad Sci U S A 2015;112:E5503-12.

Tong, Y.K. et al. Noninvasive prenatal detection of fetal trisomy 18 by epigenetic allelic ratio analysis in maternal plasma: Theoretical and empirical considerations. Clin Chem 2006;52:2194-202.

Veldore, V.H. et al. Validation of liquid biopsy: Plasma cell-free DNA testing in clinical management of advanced non-small cell lung cancer. Lung Cancer (Auckl) 2018;9:1-11.

Wong, I.H. et al. Detection of aberrant p16 methylation in the plasma and serum of liver cancer patients. Cancer Res 1999;59:71-3.

Zheng, Y.W.L. et al. Nonhematopoietically derived DNA is shorter than hematopoietically derived DNA in plasma: A transplantation model. Clin Chem 2012;58:549-58.

\* cited by examiner

TISSUE-SPECIFIC METHYLATION MARKER

CROSS-REFERENCE

This application claims priority to U.S. provisional application No. 62/643,649, filed Mar. 15, 2018, and U.S. provisional application No. 62/769,928, filed Nov. 20, 2018, each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Apr. 19, 2019, is named 50251-829_201_SL.txt and is 4,254 bytes in size.

BACKGROUND

Quantitative measurement of DNA from different tissues to circulating DNA can potentially provide important information regarding the presence of many different pathological conditions. However, existing methods involving genome-wide bisulfite sequencing are relatively expensive and may present challenges for analysis. More cost-effective approaches for measuring DNA derived from different tissues would be useful.

Detection of circulating cell-free DNA derived from cancer cells, often known as liquid biopsy, is increasingly used for the management of cancer patients. For example, the detection of epidermal growth factor receptor (EGFR) mutations in plasma can correlate well with the mutational status in the tumor tissues and can predict the responsiveness to EGFR tyrosine kinase inhibitors. In addition to point mutations, other cancer-associated genetic and genomic alterations, including copy number changes and altered fragmentation patterns could also be detected in the cell-free plasma of cancer patients. Patients identified by screening of plasma DNA can potentially have significantly earlier stage distribution and superior progression-free survival compared with patients who do not undergo screening.

SUMMARY

One aspect of the present disclosure provides a method of determining whether an organism having cancer of a first tissue has a cancer located at a second tissue, the method comprising: (a) obtaining cell-free DNA molecules from a first biological sample of the organism having cancer of a first tissue; (b) performing an assay on the cell-free DNA molecules to determine a first methylation status of a target sequence in the cell-free DNA molecules, wherein the first methylation status of the target sequence indicates that a cell-free DNA molecule comprising the target sequence is from a second tissue of the organism, wherein the first tissue and the second tissue are different; (c) determining an absolute amount of cell-free DNA molecules from the first biological sample comprising the target sequence with the first methylation status; and (d) determining whether the organism has cancer at the second tissue based on the absolute amount.

In some cases, the methylation status comprises a methylation level. In some cases, the assay comprises isolating the cell-free DNA molecule comprising the target sequence from the first biological sample. In some cases, the assay comprises isolating the cell-free DNA molecule comprising the target sequence in an oil emulsion. In some cases, the assay comprises hybridizing the cell-free DNA molecule comprising the target sequence to a probe. In some cases, the probe hybridizes to the target sequence. In some cases, an affinity of hybridization of the probe to the target sequence depends on the first methylation status of the target sequence in the first biological sample. In some cases, the probe hybridizes to the target sequence when a methylation site of the target sequence is methylated in the first biological sample. In some cases, the probe hybridizes to the target sequence when a methylation site of the target sequence is unmethylated in the first biological sample. In some cases, the assay comprises detecting the hybridization of the probe to the target sequence.

In some cases, the assay comprises amplifying the cell-free DNA molecule. In some cases, the amplifying comprises use of a pair of primers. In some cases, an affinity of hybridization of at least one primer of the pair of primers to the target sequence depends on the first methylation status of the target sequence. In some cases, the at least one primer of the pair of primers hybridizes to the target sequence when a methylation site of the target sequence is methylated in the first biological sample. In some cases, the at least one primer of the pair of primers hybridizes to the target sequence when a methylation site of the target sequence is unmethylated in the first biological sample. In some cases, the assay comprises bisulfate conversion of unmethylated cytosine residues in the cell-free DNA molecule to uracil. In some cases, the assay comprises performing methylation-aware sequencing of cell-free DNA molecules from the first biological sample.

In some cases, the target sequence comprises at least 3, at least 4, at least 5, at least 6, at least 7, at least 8, at least 9, or at least 10 methylation sites. In some cases, the target sequence comprises at least 5 methylation sites. In some cases, the first methylation status comprises methylation density for individual sites within the target sequence, a distribution of methylated/unmethylated sites over a contiguous region within the target sequence, a pattern or level of methylation for each individual methylation site within the target sequence, or non-CpG methylation. In some cases, the target sequence comprises a higher methylation density in the first tissue than in the second tissue. In some cases, the first methylation status comprises methylation density for individual sites with the target sequence, and the target sequence has a methylation density in the first tissue that is at least 50%, at least 60%, at least 70%, at least 80%, at least 90%, or at least 95%. In some cases, the target sequence comprises a methylation density in the first tissue that is more than 50%. In some cases, the target sequence comprises a methylation density in the second tissue that is at most 50%, at most 40%, at most 30%, at most 20%, at most 10%, at most 5%, or 0%. In some cases, the target sequence comprises a methylation density in the second tissue that is less than 20%. In some cases, the target sequence comprises a lower methylation density in the first tissue than in the second tissue. In some cases, the target sequence comprises a methylation density in the first tissue that is at most 50%, at most 40%, at most 30%, at most 20%, at most 10%, at most 5%, or 0%. In some cases, the target sequence comprises a methylation density in the first tissue that is less than 50%. In some cases, the target sequence comprises a methylation density in the second tissue that is at least 50%, at least 60%, at least 70%, at least 80%, at least 90%, at least 95%, or 100%. In some cases, the target sequence comprises a methylation density in the second tissue that is more than 80%.

In some cases, the first tissue comprises liver tissue, and the target sequence comprises a polynucleotide sequence having at least 60%, 70%, 80%, 90%, 95%, 98%, or 99% identity to SEQ ID NO: 1. In some cases, the first tissue comprises liver tissue, and wherein the assay comprises amplification using a primer comprising SEQ ID NO: 2, a primer comprising SEQ ID NO: 3, or both, or use of a detectably-labeled probe comprising SEQ ID NO: 4 for detection of the target sequence. In some cases, the amplification further comprises use of a primer comprising SEQ ID NO: 5, a primer comprising SEQ ID NO: 6, or both, or use of a detectably-labeled probe comprising SEQ ID NO: 7 for detection of the target sequence.

In some cases, the first tissue comprises colon tissue, and the target sequence comprises a polynucleotide sequence having at least 60%, 70%, 80%, 90%, 95%, 98%, or 99% identity to SEQ ID NO: 8. In some cases, the first tissue comprises colon tissue, and wherein the amplification comprises use of a primer comprising SEQ ID NO: 9, a primer comprising SEQ ID NO: 10, or both, or use of a detectably-labeled probe comprising SEQ ID NO: 11 for detection of the target sequence. In some cases, the methylation-specific amplification further comprises use of a primer comprising SEQ ID NO: 12, a primer comprising SEQ ID NO: 13, or both, or use of a detectably-labeled probe comprising SEQ ID NO: 14 for detection of the target sequence.

In some cases, the cancer is selected from the group consisting of: bladder cancer, bone cancer, brain tumor, breast cancer, carcinoma of cervix, colorectal cancer, esophageal cancer, gastrointestinal cancer, hematopoietic malignancy, head and neck squamous cell carcinoma, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, melanoma, and thyroid cancer. In some cases, the cancer comprises hepatocellular carcinoma or colorectal carcinoma.

In some cases, the method further comprises determining a classification of the cancer in the second tissue. In some cases, the determining the classification of cancer in the second tissue comprises assessing cell-free nucleic acid molecules from a second biological sample from the organism. In some cases, the assessing comprises determining methylation profile, copy number variations, single polymorphism (SNP) profile, or fragmentation pattern of the cell-free nucleic acid molecules from the second biological sample. In some cases, the assessing comprises determining an amount of cell-free nucleic acid molecules from the second biological sample that are from a pathogen. In some cases, the second biological sample is same as the first biological sample. In some cases, wherein the second biological sample is different than the first biological sample.

One aspect of the present disclosure provides a system configured to perform the method as provided herein.

One aspect of the present disclosure provides a non-transitory computer-readable medium comprising a series of instructions for controlling a computer system to perform the method as disclosed herein.

One aspect of the present disclosure provides a method of analyzing a biological sample of an organism. The method can comprise: amplifying a first tissue-specific marker in a cell-free DNA molecule from the biological sample based on methylation status of the first tissue-specific marker, wherein the first tissue-specific marker comprises a predetermined sequence with one or more differentiated methylation sites having a first methylation status in a first tissue of the organism and a second methylation status in other tissues of the organism, and wherein the first and second methylation statuses are different; identifying a tissue of origin for the cell-free DNA molecule by detecting the amplification of the first tissue-specific marker; and determining an absolute amount of cell-free DNA molecules from the biological sample that are from the first tissue of the organism.

In some cases, the method further comprises bisulfate conversion of unmethylated cytosine residues to uracil before the amplification. In some cases, the method further comprises isolating the cell-free DNA molecule from other DNA molecules from the biological sample before the amplification. In some cases, the amplification comprises use of a methylation-specific primer complementary to the first tissue-specific marker and annealing to at least a portion of the one or more differentiated methylation sites. In some cases, the identifying the tissue of origin comprises determining that the cell-free DNA molecule is from the first tissue if the first tissue-specific marker in the cell-free DNA molecule is amplified by primers that are configured to amplify first tissue-specific marker methylated at the first methylation status.

In some cases, the one or more differentiated methylation sites have a higher methylation density in the first tissue than in the second tissue. In some cases, the one or more differentiated methylation sites have a methylation density in the first tissue that is at least 50%, at least 60%, at least 70%, at least 80%, at least 90%, or at least 95%. In some cases, the one or more differentiated methylation sites have a methylation density in the first tissue that is more than 50%. In some cases, the one or more differentiated methylation sites have a methylation density in the second tissue that is at most 50%, at most 40%, at most 30%, at most 20%, at most 10%, at most 5%, or 0%. In some cases, the one or more differentiated methylation sites have a methylation density in the second tissue that is less than 20%.

In some cases, the one or more differentiated methylation sites have a lower methylation density in the first tissue than in the second tissue. In some cases, the one or more differentiated methylation sites have a methylation density in the first tissue that is at most 50%, at most 40%, at most 30%, at most 20%, at most 10%, at most 5%, or 0%. In some cases, the one or more differentiated methylation sites have a methylation density in the first tissue that is less than 50%. In some cases, the one or more differentiated methylation sites have a methylation density in the second tissue that is at least 50%, at least 60%, at least 70%, at least 80%, at least 90%, at least 95%, or 100%. In some cases, the one or more differentiated methylation sites have a methylation density in the second tissue that is more than 80%.

In some cases, the first tissue comprises liver tissue, and the first tissue-specific marker comprises a polynucleotide sequence having at least 60%, 70%, 80%, 90%, 95%, 98%, or 99% identity to SEQ ID NO: 1. In some cases, the first tissue comprises liver tissue, and wherein the amplification comprises use of a primer comprising SEQ ID NO: 2, a primer comprising SEQ ID NO: 3, or both, or use of a detectably-labeled probe comprising SEQ ID NO: 4 for detection of the first tissue-specific marker. In some cases, the amplification further comprises use of a primer comprising SEQ ID NO: 5, a primer comprising SEQ ID NO: 6, or both, or use of a detectably-labeled probe comprising SEQ ID NO: 7 for detection of the first tissue-specific marker. In some cases, the first tissue comprises colon tissue, and the first tissue-specific marker comprises a polynucleotide sequence having at least 60%, 70%, 80%, 90%, 95%, 98%, or 99% identity to SEQ ID NO: 8. In some cases, the first tissue comprises colon tissue, and wherein the amplification comprises use of a primer comprising SEQ ID NO:9, a primer comprising SEQ ID NO: 10, or both, or use of a detectably-labeled probe comprising SEQ ID NO: 11 for detection of the first tissue-specific marker. In some cases, the methylation-specific amplification further comprises use of a primer comprising SEQ ID NO: 12, a primer comprising SEQ ID NO: 13, or both, or use of a detectably-labeled probe comprising SEQ ID NO: 14 for detection of the first tissue-specific marker.

In some cases, the method further comprises determining an amount of cell-free DNA molecules from the biological sample that are derived from a second tissue based on methylation pattern of a second tissue-specific marker, wherein the first and second tissues are different. In some cases, the second tissue belongs to the organism.

In some cases, the method further comprises diagnosing, monitoring, or prognosticating a cancer in the first tissue based on the absolute amount of the cell-free DNA molecules from the biological sample that are from the first tissue of the organism. In some cases, the cancer is selected from the group consisting of: bladder cancer, bone cancer, brain tumor, breast cancer, carcinoma of cervix, colorectal cancer, esophageal cancer, gastrointestinal cancer, hematopoietic malignancy, head and neck squamous cell carcinoma, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, melanoma, and thyroid cancer. In some cases, the cancer comprises hepatocellular carcinoma or colorectal carcinoma. In some cases, the diagnosing or monitoring comprises determining the size of a tumor in the first tissue based on the absolute amount of the cell-free DNA molecules from the biological sample that are from the first tissue of the organism. In some cases, the diagnosing or monitoring comprises determining whether the cancer has metastasized to the first tissue based on the absolute amount of the cell-free DNA molecules from the biological sample that are from the first tissue of the organism.

In some cases, the first tissue comprises a transplanted organ. In some cases, the method provided herein further comprises assessing organ transplant based on the absolute amount of the cell-free DNA molecules from the biological sample that are from the first tissue.

Another aspect of the present disclosure provides a composition for determining amount of cell-free DNA molecules from a biological sample that are from liver of an organism. The composition can comprise a pair of primers for amplification of a liver-specific marker based on methylation status of the liver-specific marker, wherein the liver-specific marker comprises a polynucleotide sequence having at least 60%, 70%, 80%, 90%, 95%, 98%, or 99% identity to SEQ ID NO: 1. In some cases, the pair of primers comprises a primer comprising SEQ ID NO: 2, and a primer comprising SEQ ID NO: 3. In some cases, the composition further comprises a detectably-labeled probe comprising SEQ ID NO: 4 for detection of the liver-specific marker. In some cases, the composition further comprises a primer comprising SEQ ID NO: 5 and a primer comprising SEQ ID NO: 6. In some cases, the composition further comprises a detectably-labeled probe comprising SEQ ID NO: 7 for detection of the liver-specific marker.

Another aspect of the present disclosure provides a composition for determining amount of cell-free DNA molecules from a biological sample that are from colon of an organism, comprising a pair of primers for amplification of a colon-specific marker based on methylation status of the colon-specific marker, wherein the colon-specific marker comprises a polynucleotide sequence having at least 60%, 70%, 80%, 90%, 95%, 98%, or 99% identity to SEQ ID NO: 8. In some cases, the pair of primers comprises a primer comprising SEQ ID NO: 9, and a primer comprising SEQ ID NO: 10. In some cases, the composition further comprises a detectably-labeled probe comprising SEQ ID NO: 11 for detection of the colon-specific marker. In some cases, the composition further comprises a primer comprising SEQ ID NO: 12 and a primer comprising SEQ ID NO: 13. In some cases, the composition further comprises a detectably-labeled probe comprising SEQ ID NO: 14 for detection of the colon-specific marker.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

(FIG. 5A) absolute concentration of colon-derived DNA, (FIG. 5B) fractional concentration of colon-derived DNA, (FIG. 5C) absolute concentration of liver-derived DNA, and (FIG. 5D) fractional concentration of liver-derived DNA.

DETAILED DESCRIPTION

Figure 1:
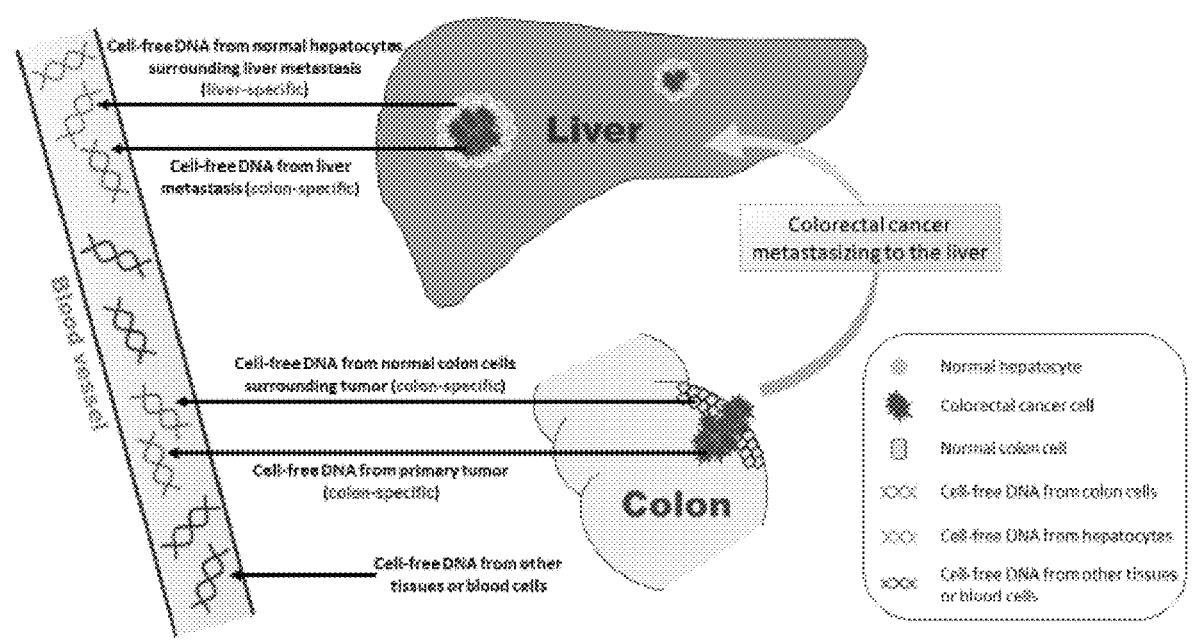
FIG. 1 is a schematic drawing of plasma cell-free DNA origins in patients with colorectal cancer with liver metastasis.

Provided herein are methods, compositions, and systems for quantifying cell-free nucleic acid molecules, e.g., cell-free DNA molecules, e.g., plasma DNA, that are from specific tissues using tissue-specific markers. Also provided herein are clinical applications of these markers, for instance, but not limited to, in diagnosis, monitoring, and prognostication of cancer, in detection of metastatic cancer, and in some case, in assessment of organ transplantation.

In addition to cancer-specific changes, there can be a general increase in DNA released from an organ affected by a cancer into the circulation. For instance, the level of liver-derived DNA can be increased in liver cancer patients. Without wishing to be bound by a certain theory, the increased level of DNA released by the organ affected by the cancer can be due to the direct release of DNA from the tumor cells or the increased turnover of non-tumor cells invaded by the cancer. Such an increase in release of tissue specific DNA can also be observed in organ transplant recipients who experienced acute rejection as a result of increased cell turnover. In some cases, the proportional contribution of the cells within the transplanted organ into plasma DNA determined by methylation deconvolution correlates well with that determined based on the analysis of donor-specific alleles.

In some cases, methylation deconvolution using genome-wide bisulfite sequencing can be challenging because of the relatively high cost and long turn-around time. Moreover, in some cases, methylation deconvolution can determine the relative or proportional contributions of different organs rather than the absolute concentration of DNA derived from each organ. In scenarios where DNA from more than one organ would be released into the circulation, the measurement of absolute concentration of DNAs derived from a specific organ can be more informative. For example, in a patient with colorectal cancer (CRC) metastasizing to the liver, an increased amount of DNA would be released from the liver into the circulation. However, the fraction of liver DNA in plasma might show a paradoxical reduction because of the even larger degree of increase in DNA released by the tumor cells which have originated from the colon. Therefore, the development of a method that can accurately determine the absolute amount of DNA with a tissue-specific methylation pattern can be useful.

I. Tissue-Specific Marker

Provided herein are tissue-specific markers that can identify a tissue of origin for a cell-free DNA molecule. In some cases, the tissue-specific marker is a polynucleotide sequence of the genome of an organism. In some cases, the tissue-specific marker comprises a differentiated methylated region (DMR) which is identified based on the methylation status of one or more differentiated methylation sites contained within the marker polynucleotide sequence. In some cases, the one or more differentiated methylation sites comprise one or more CpG sites. In some cases, the one or more differentiated methylation sites comprise one or more non-CpG sites. In some cases, a tissue-specific marker as discussed herein can be referred to as a target sequence.

In some cases, the differentiated methylation sites of the tissue-specific marker have a first methylation status in a first tissue of the organism, whereas a second methylation status in a different second tissue of the organism. The first and second methylation statuses can be different so that the first and second tissues can be differentiated based on the methylation status of the tissue-specific marker.

In some cases, the differentiated methylation sites of the tissue-specific marker have a first methylation status in a first tissue of the organism, whereas a second methylation status in all other tissues of the organism. The first and second methylation statuses can be different so that the first tissue can be differentiated from all other tissues of the organism based on the methylation status of the tissue-specific marker.

In some cases, the tissue-specific marker comprises at least 1, at least 2, at least 3, at least 4, at least 5, at least 6, at least 7, at least 8, at least 9, at least 10, at least 12, at least 15, at least 20, at least 25, at least 30, at least 50 differentiated methylation sites. In some cases, the tissue-specific marker comprises at least 5 differentiated methylation sites. A methylated nucleotide or a methylated nucleotide base can refer to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. In this case, cytosine is not a methylated nucleotide and 5-methylcytosine is a methylated nucleotide. In another example, thymine contains a methyl moiety at position 5 of its pyrimidine ring, however, for purposes herein, thymine is not considered a methylated nucleotide when present in DNA since thymine is a typical nucleotide base of DNA. Typical nucleoside bases for DNA are thymine, adenine, cytosine and guanine. Typical bases for RNA are uracil, adenine, cytosine and guanine. Correspondingly a "methylation site" can be the location in the target gene nucleic acid region where methylation has, or has the possibility of occurring. For example a location containing CpG is a methylation site wherein the cytosine may or may not be methylated. A "site" can correspond to a single site, which can be a single base position or a group of correlated base positions, e.g., a CpG site. A methylation site can refer to a CpG site, or a non-CpG site of a DNA molecule that has the potential to be methylated. A CpG site can be a region of a DNA molecule where a cytosine nucleotide is followed by a guanine nucleotide in the linear sequence of bases along its 5' to 3' direction and that is susceptible to methylation either by natural occurring events in vivo or by an event instituted to chemically methylate the nucleotide in vitro. A non-CpG site can be a region that does not have a CpG dinucleotide sequence but is also is susceptible to methylation either by natural occurring events in vivo or by an event instituted to chemically methylate the nucleotide in vitro. A locus or region can correspond to a region that includes multiple sites.

The methylation status of the tissue-specific maker can comprise methylation density for individual sites within the marker region, a distribution of methylated/unmethylated sites over a contiguous region within the marker, a pattern or level of methylation for each individual methylation site within the marker that contains more than one sites, and non-CpG methylation. In some cases, the methylation status of the tissue-specific maker comprises methylation level (or methylation density) for individual differentiated methylation sites. The methylation density can refer to, for a given methylation site, a fraction of nucleic acid molecules methylated at the given methylation site over the total number of nucleic acid molecules of interest that contain such methylation site. For instance, the methylation density of a first methylation site in liver tissue can refer to a fraction of liver DNA molecules methylated at the first site over the total liver DNA molecules. In some cases, the methylation status comprises coherence of methylation/unmethylation status among individual differentiated methylation sites.

In some cases, the tissue-specific marker comprises methylation sites that are hypermethylated in a first tissue, but are hypomethylated in a second tissue. For instance, the tissue-specific marker can comprise one or more methylation sites that are hypermethylated in liver tissue, by which it can mean the one or more methylation sites have an at least 50%, at least 60%, at least 70%, at least 80%, at least 90%, or at least 95% methylation density in liver tissue; in contrast, the one or more methylation sites can have an at most 50%, at most 40%, at most 30%, at most 20%, at most 10%, at most 5%, or 0% methylation density in other tissues, such as, but not limited to, blood cells, lung, esophagus, stomach, small intestines, colon, pancreas, urinary bladder, heart, and brain. The tissue-specific marker can comprise at least 1, at least 2, at least 3, at least 4, at least 5, at least 6, at least 7, at least 8, at least 9, at least 10, at least 12, at least 15, at least 20, at least 25, at least 30, at least 50 methylation sites that are hypermethylated in a first tissue, but hypomethylated in a second tissue. In some cases, the tissue-specific marker comprises at least 5 methylation sites that are hypermethylated in a first tissue, but hypomethylated in a second tissue.

The tissue-specific marker can comprise at most 300 base-pairs (bp), at most 250 bp, at most 225 bp, at most 200 bp, at most 190 bp, at most 185 bp, at most 180 bp, at most 175 bp, at most 170 bp, at most 169 bp, at most 168 bp, at most 167 bp, at most 166 bp, at most 165 bp, at most 164 bp, at most 163 bp, at most 162 bp, at most 161 bp, at most 160 bp, at most 150 bp, at most 140 bp, at most 120 bp, or at most 100 bp. In some cases, the tissue-specific marker comprises at most 166 bp.

In some cases, the liver-specific marker as provided herein comprises at least 1, at least 2, at least 3, at least 4, at least 5, at least 6, at least 7, at least 8, at least 9, at least 10, at least 12, at least 15, at least 20, at least 25, at least 30, at least 50 methylation sites that are hypermethylated in liver tissue, but hypomethylated in other tissues. In some cases, the liver-specific marker as provided herein comprises at least 5 methylation sites that are hypermethylated in liver tissue, but hypomethylated in other tissues. Each of the methylation sites that are hypermethylated in liver tissue can have an at least 50%, at least 60%, at least 70%, at least 80%, at least 90%, or at least 95% methylation density in liver tissue, and an at most 50%, at most 40%, at most 30%, at most 20%, at most 10%, at most 5%, or 0% methylation density in other tissues, such as, but not limited to, blood, brain, thymus, pancreas, kidney. In some cases, each of the methylation sites that are hypermethylated in liver tissue can have a more than 50% methylation density in liver tissue, and a less than 20% methylation density in other tissues, such as, but not limited to, blood cells, lung, esophagus, stomach, small intestines, colon, pancreas, urinary bladder, heart, and brain.

In some cases, the tissue-specific marker comprises methylation sites that are hypomethylated in a first tissue, but are hypermethylated in a second tissue. In some cases, the tissue-specific marker comprises methylation sites that are hypomethylated in a first tissue, but are hypermethylated in other tissues. For instance, the tissue-specific marker can comprise one or more methylation sites that are hypomethylated in liver tissue, by which it can mean the one or more methylation sites have an at most 50%, at most 40%, at most 30%, at most 20%, at most 10%, at most 5%, or 0% methylation density in liver tissue; in contrast, the one or more methylation sites can have an at least 50%, at least 60%, at least 70%, at least 80%, at least 90%, or at least 95% methylation density in other tissues, such as, but not limited to, blood cells, lung, esophagus, stomach, small intestines, colon, pancreas, urinary bladder, heart, and brain. The tissue-specific marker can comprise at least 1, at least 2, at least 3, at least 4, at least 5, at least 6, at least 7, at least 8, at least 9, at least 10, at least 12, at least 15, at least 20, at least 25, at least 30, at least 50 methylation sites that are hypomethylated in a first tissue, but hypermethylated in a second tissue. In some cases, the tissue-specific marker comprises at least 5 methylation sites that are hypomethylated in a first tissue, but hypermethylated in a second tissue.

In some cases, the liver-specific marker as provided herein comprises at least 1, at least 2, at least 3, at least 4, at least 5, at least 6, at least 7, at least 8, at least 9, at least 10, at least 12, at least 15, at least 20, at least 25, at least 30, at least 50 methylation sites that are hypomethylated in liver tissue, but hypermethylated in other tissues. In some cases, the liver-specific marker as provided herein comprises at least 5 methylation sites that are hypomethylated in liver tissue, but hypermethylated in other tissues. Each of the methylation sites that are hypomethylated in liver tissue can have an at most 50%, at most 40%, at most 30%, at most 20%, at most 10%, or at most 5% methylation density in liver tissue, and an at least 50%, at least 60%, at least 70%, at least 80%, at least 90%, at least 95%, or 100% methylation density in other tissues, such as, but not limited to, blood, brain, thymus, pancreas, kidney. In some cases, each of the methylation sites that are hypomethylated in liver tissue can have a less than 50% methylation density in liver tissue, and a more than 80% methylation density in other tissues, such as, but not limited to, blood cells, lung, esophagus, stomach, small intestines, colon, pancreas, urinary bladder, heart, and brain.

In some cases, the colon-specific marker as provided herein comprises at least 1, at least 2, at least 3, at least 4, at least 5, at least 6, at least 7, at least 8, at least 9, at least 10, at least 12, at least 15, at least 20, at least 25, at least 30, at least 50 methylation sites that are hypermethylated in colon tissue, but hypomethylated in other tissues. In some cases, the colon-specific marker as provided herein comprises at least 5 methylation sites that are hypermethylated in colon tissue, but hypomethylated in other tissues. Each of the methylation sites that are hypermethylated in colon tissue can have an at least 50%, at least 60%, at least 70%, at least 80%, at least 90%, or at least 95% methylation density in colon tissue, and an at most 50%, at most 40%, at most 30%, at most 20%, at most 10%, at most 5%, or 0% methylation density in other tissues, such as, but not limited to, blood, brain, thymus, pancreas, kidney. In some cases, each of the methylation sites that are hypermethylated in colon tissue can have a more than 50% methylation density in colon tissue, and a less than 20% methylation density in other tissues, such as, but not limited to, blood cells, lung, esophagus, stomach, small intestines, liver, pancreas, urinary bladder, heart, and brain.

In some cases, the colon-specific marker as provided herein comprises at least 1, at least 2, at least 3, at least 4, at least 5, at least 6, at least 7, at least 8, at least 9, at least 10, at least 12, at least 15, at least 20, at least 25, at least 30, at least 50 methylation sites that are hypomethylated in colon tissue, but hypermethylated in other tissues. In some cases, the colon-specific marker as provided herein comprises at least 5 methylation sites that are hypomethylated in colon tissue, but hypermethylated in other tissues. Each of the methylation sites that are hypomethylated in colon tissue can have an at most 50%, at most 40%, at most 30%, at most 20%, at most 10%, or at most 5% methylation density in colon tissue, and an at least 50%, at least 60%, at least 70%, at least 80%, at least 90%, at least 95%, or 100% methylation density in other tissues, such as, but not limited to, blood, brain, thymus, pancreas, kidney. In some cases, each of the methylation sites that are hypomethylated in colon tissue can have a less than 50% methylation density in colon tissue, and a more than 80% methylation density in other tissues, such as, but not limited to, blood cells, lung, esophagus, stomach, small intestines, liver, pancreas, urinary bladder, heart, and brain.

Also provided herein is a liver-specific marker for identifying liver-derived DNA molecules. A liver-specific marker can be located in the exonic region of the protein tyrosine kinase 2 beta (PTK2B) gene on chromosome 8. The eight CpG sites within the liver-specific DMR can be hypermethylated in the liver but hypomethylated in other tissues and blood cells. A liver-specific marker as provided herein can comprise a polynucleotide sequence having at least about 50%, 60%, 70%, 80%, 90%, 95%, 98%, or 99% identity to SEQ ID NO: 1. A liver-specific marker as provided herein can comprise SEQ ID NO: 1.

Also provided herein is a colon-specific marker for identifying colon-derived DNA molecules. A colon-specific marker can be located in the exonic region of the Sestrin 3 (SESN3) gene on chromosome 11. All the six CpG sites located within the colon-specific DMR can be hypermethylated in the colon but hypomethylated in other tissues and blood cells. A colon-specific marker can comprise a polynucleotide sequence having at least about 50%, 60%, 70%, 80%, 90%, 95%, 98%, or 99% identity to SEQ ID NO: 8.

As used herein, the term "identity" or "percent identity" between two or more nucleotide or amino acid sequences can be determined by aligning the sequences for optimal comparison purposes (e.g., gaps can be introduced in the sequence of a first sequence). The nucleotides at corresponding positions can then be compared, and the percent identity between the two sequences can be a function of the number of identical positions shared by the sequences (i.e., % identity=# of identical positions/total # of positions×100). For example, a position in the first sequence may be occupied by the same nucleotide as the corresponding position in the second sequence, then the molecules are identical at that position. The percent identity between the two sequences may be a function of the number of identical positions shared by the sequences, taking into account the number of gaps, and the length of each gap, which need to be introduced for optimal alignment of the two sequences. In some cases, the length of a sequence aligned for comparison purposes is at least about: 30%, 40%, 50%, 60%, 65%, 70%, 75%, 80%, 85%, 90%, 91%, 92%, 93%, 94%, 95%, 96%, 97%, 98%, or 95%, of the length of the reference sequence. A BLAST® search can determine homology between two sequences. The homology can be between the entire lengths of two sequences or between fractions of the entire lengths of two sequences. The two sequences can be genes, nucleotides sequences, protein sequences, peptide sequences, amino acid sequences, or fragments thereof. The actual comparison of the two sequences can be accomplished by well-known methods, for example, using a mathematical algorithm. A non-limiting example of such a mathematical algorithm can be those described in Karlin, S. and Altschul, S., Proc. Natl. Acad. Sci. USA, 90-5873-5877 (1993). Such an algorithm can be incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA.

Also provided herein are methods of identifying tissue-specific markers. The method can comprise comparing methylation status across the genome among different tissue samples. Publicly available databases, such as, databases from RoadMap Epigenomics Project (Roadmap Epigenomics Consortium et al. Nature 2015; 518:317-30) and BLUEPRINT project (Martens et al. Haematologica 2013; 98:1487-9), can be utilized for bioinformatics analysis in order to screen for potential tissue-specific markers. In some cases, experimental validation is desirable. For instance, methylation-aware sequencing, such as bisulfite sequencing, can be performed to validate the methylation status among different tissues. In some cases, methylation-specific amplification can also be used for a relatively more target-orientated validation.

II. Methods of Analyzing Cell-Free DNA Molecules from a Tissue

Provided herein are methods of analyzing a biological sample of an organism. A method as provided herein can determine an absolute amount of cell-free nucleic acid molecules, e.g., cell-free DNA molecules, from a tissue of an organism. A method can comprise identifying a cell-free DNA molecule from a biological sample as a cell-free DNA molecule from a first tissue of the organism when the cell-free DNA molecule comprises a first tissue-specific marker having a first methylation status. In some cases, the first tissue-specific marker comprises a predetermined sequence with one or more differentiated methylation sites. In some cases, the first tissue-specific marker can have a first methylation status in a first tissue and a second methylation status in other tissues of the organism, and the first methylation status and the second methylation status can be different.

As provided herein, a method can comprise assessing methylation status of a cell-free DNA molecule. In some cases, a method can further comprise bisulfate conversion of unmethylated cytosine residues to uracil before the amplification. In some cases, a method can comprise conversion of either methylated or unmethylated cytosine residues by any other method, so that the converted residues can be differentiated by the subsequent detection method, e.g. primer-based amplification. In some cases, the cell-free DNA molecule can be digested with a methylation-sensitive enzyme that digests a DNA molecule at one or more specific methylation sites when the methylation sites are methylated or unmethylated. The methylation-sensitive enzyme can thus be used to differentiate methylated and unmethylated DNA molecules. Non-limiting examples of methylation-sensitive enzymes that can be used in the methods provided herein can include Aat II, Acc II, Aor13H I, Aor51H I, BspT104 I, BssH II, Cfr10 I, Cla I, Cpo I, Eco52 I, Hae II, Hap II, Hha I, Mlu I, Nae I, Not I, Nru I, Nsb I, PmaC I, Psp1406 I, Pvu I, Sac II, Sal I, Sma I, SnaB I, and any combinations thereof.

A method as provided herein can comprise amplifying a first tissue-specific marker in a cell-free DNA molecule from the biological sample based on the methylation status of the first tissue-specific marker. The method can further comprise identifying a tissue of origin for the cell-free DNA molecule by detecting the amplification of the first tissue-specific marker. A method can further comprise determining an absolute amount of cell-free DNA molecules from the biological sample that are from the first tissue of the organism. Amplification reaction can refer to a process for copying nucleic acid one or more times. In some cases, the method of amplification includes but is not limited to polymerase chain reaction (PCR), self-sustained sequence reaction, ligase chain reaction, rapid amplification of cDNA ends, polymerase chain reaction and ligase chain reaction, Q-beta phage amplification, strand displacement amplification, or splice overlap extension polymerase chain reaction. In some cases, a single molecule of nucleic acid is amplified, for example, by digital PCR.

In some cases, the amplification comprises use of a methylation-specific primer complementary to the first tissue-specific marker and annealing to at least a portion of the one or more methylation sites. A methylation-specific primer can refer to a primer that can differentiate methylated and unmethylated target sequence. For a given target sequence that contains methylation sites, a methylation-specific primer can be designed to cover at least a portion of the methylation sites. In some cases, when bisulfite conversion is performed before amplification, the nucleotide residue on the methylation-specific primer for a given methylation site can be designed to be complementary to unconverted cytosine residue at the site for detecting methylated target sequence, whereas for detecting unmethylated target sequence, the nucleotide residue on the methylation-specific primer can be designed to be complementary to converted residue at the site (e.g. uracil residue).

In some cases, a method can further comprise isolating the cell-free DNA molecule from other DNA molecules from the biological sample before the amplification. By physically isolating the cell-free DNA molecule, a "digital" assay of the cell-free DNA molecules from the biological sample can be performed, such as, but not limited to, digital PCR, e.g. droplet digital PCR. The isolation method can be any method known to a skilled artisan, such as, but not limited to, isolation by micro well plates, capillaries, oil emulsion, and arrays of miniaturized chambers. The digital PCR reaction can be performed using any known techniques in the art, such as, microfluidics-based, or emulsion-based, e.g. BEAMing (Dressman et al. *Proc Natl Acad Sci USA* 2003; 100: 8817-8822).

In some cases, the first tissue comprises liver tissue, and the method comprises use of a liver-specific marker as discussed above. In some cases, the liver-specific marker, e.g. SEQ ID NO: 1, comprises sites hypermethylated in liver but hypomethylated in other tissues. In these cases, the method can comprise primers for detecting methylated liver tissue-specific marker ("primers for methylated assay"). For instance, the primers for methylated assay can comprise a primer comprising SEQ ID NO: 2, a primer comprising SEQ ID NO: 3, or both. In some cases, the primers provided herein are used for amplification reactions after bisulfite conversion. Alternatively or cumulatively, the method can comprise use of a detectably-labeled probe comprising SEQ ID NO: 4, for detection of the methylated liver tissue-specific marker. Optionally, the method can further comprise use of primers for detecting unmethylated liver tissue-specific marker ("primers for unmethylated assay"). The primers for unmethylated assay can comprise a primer comprising SEQ ID NO: 5, a primer comprising SEQ ID NO: 6, or both. Alternatively or cumulatively, the method can comprise use of a detectably-labeled probe comprising SEQ ID NO: 7, for detection of the unmethylated liver tissue-specific marker.

A primer, a probe, or an oligonucleotide, can be used interchangeably herein and can refer to a polymer of more than one, e.g., 2, 4, 6, 8, 10, 14, 18, 20, or 40 nucleotides or chemically modified nucleotides that are linked together via phosphodiester bond. A primer can comprise about 20 to about 30 nucleotides. A primer can comprise at least 6, 8, 10, 12, 14, 16, 18, 20, 22, 24, 26, 28, 30, 32, 34, 36, 38, or 40 nucleotides. Chemical modifications to the constitute nucleotides of a primer can be introduced to modify certain properties of the primer, for instance, increasing its stability, increasing hybridization specificity, and labeling with a detectable signal. Chemical modifications that can be used in the compositions provided herein can include covalent modifications, attachment chemistry, and modification of nucleotide bases. Chemical modifications can include phosphorylation, addition of biotin, cholesteryl-TEG, amino-modifiers (e.g., C6, C12, or dT), azide, alkyne, thiol modifiers, fluorophore, dark quencher, and spacer. A primer can comprise one or more phosphorothioate bonds, or one or more modified bases, such as 2-aminopurine, 2,6-di-aminopurine (2-amino-dA), 5-bromo dU, deoxyUridine, inverted dT, inverted dideoxy-T, dideoxy-C, 5-methyl dC, deoxyinoside, super T®, super G®, locked nucleic acids, 5-nitroindole, 2'-O-methyl RNA bases, hydroxymethyl dC, iso-dC, iso-dG, fluoro bases (e.g., fluoro C, U, A, G, T), and 2'-O-methoxy-ethyl bases (e.g., 2-methoxyethoxy A, G, U, C, T). The detectably-labeled probe can comprise any detectable label known to one skilled in the art, for instance, any suitable fluorophore. The PCR reaction (e.g., digital PCR or real-time PCR) can be monitored via any suitable optical methods, magnetic methods, electronic methods, or any other techniques available to one of skill in the art.

In some cases, the first tissue comprises colon tissue, and the method comprises use of a colon-specific marker as discussed above. In some cases, the colon-specific marker, e.g. SEQ ID NO: 8, comprises sites hypermethylated in colon but hypomethylated in other tissues. In these cases, the primers for methylated assay can comprise a primer comprising SEQ ID NO: 9, a primer comprising SEQ ID NO: 10, or both. In some cases, the primers provided herein are used for amplification reactions after bisulfate conversion. Alternatively or cumulatively, the method can comprise use of a detectably-labeled probe comprising SEQ ID NO: 11, for detection of the methylated colon-specific marker. Optionally, the method can further comprise use of primers for detecting unmethylated colon-specific marker ("primers for unmethylated assay"). The primers for unmethylated assay can comprise a primer comprising SEQ ID NO: 12, a primer comprising SEQ ID NO: 13, or both. Alternatively or cumulatively, the method can comprise use of a detectably-labeled probe comprising SEQ ID NO: 14, for detection of the unmethylated colon-specific marker.

The methods provided herein, e.g. use of digital PCR technique, can allow the direct determination of the actual number of the target DNA molecules without the need of calibrators. Other technologies, such as certain sequencing-based methods, such as, but not limited to, bisulfite sequencing and non-bisulfite-based methylation-aware sequencing using the PacBio sequencing platform, can determine the relative or fractional concentration of the DNA from the target tissues in relation to other tissues. The absolute amount can refer to an absolute count of DNA molecules, or in some cases, can also refer to a concentration of DNA molecules, e.g., number, mole, or weight per volume, e.g., copies/mL, mole/L, or mg/L. The analysis of the absolute amount as provided herein can be useful in scenarios when increased amounts of DNA would be released from more than one type of tissues. Methylation deconvolution analysis, based on sequencing of cell-free nucleic acid molecules, such as disclosed in U.S. patent application Ser. No. 14/803,692, on the other hand, can provide readout of tissue of origin of cell-free nucleic acids in the form of fractional contribution, e.g., a first tissue contributes A % of cell-free nucleic acids from a biological sample, and a second tissue contributes B % of cell-free nucleic acids from the same biological sample.

In some cases, the methods, compositions, and systems provided herein can also make use of technologies like, real-time PCR, sequencing and microarray for methylation analysis of cell-free nucleic acids. In some cases, the absolute number of cell-free nucleic acids harboring a tissue-specific marker, such as counting positive reactions in a digital PCR assay, may not be derived directly from methylation analysis by some technologies. However, such absolute number can be calculated indirectly based on concentrations (relative or fractional) of cell-free nucleic acids harboring tissue-specific markers, for instance, by taking the total number or concentration of cell-free nucleic acids in a given volume of biological sample into account. In some cases, the sequencing that can be used in the methods provided herein can include chain termination sequencing, hybridization sequencing, Illumina sequencing (e.g., using reversible terminator dyes), ion torrent semiconductor sequencing, mass spectrophotometry sequencing, massively parallel signature sequencing (MPSS), Maxam-Gilbert sequencing, nanopore sequencing, polony sequencing, pyrosequencing, shotgun sequencing, single molecule real time (SMRT) sequencing, SOLiD sequencing (hybridization using four fluorescently labeled di-base probes), universal sequencing, or any combination thereof. Microarrays having probes targeting methylation sites can also be used for analyzing methylation status of the cell-free DNA molecules in the methods provided herein.

In some cases, the method provided herein further comprises determining an amount of cell-free DNA molecules from the biological sample that are derived from a second tissue based on methylation pattern of a second tissue-specific marker, wherein the first and second tissues are different. The second tissue can belong to the same organism. The second tissue can also come from a different organism, for instance, a fetus within a pregnant woman.

III. Methods of Diagnosing, Monitoring, Prognosticating Cancer

Provided herein are methods of diagnosing, monitoring, prognosticating cancer. A method can comprise determining an absolute amount of cell-free DNA molecules from a first tissue as discussed above, and diagnosing, monitoring, prognosticating a cancer in the first tissue based on the absolute amount of the cell-free DNA molecules from the biological sample that are from the first tissue of the organism.

An absolute amount of cell-free DNA molecules that are from a first tissue can be correlated with a condition of the first tissue. For instance, the amount of liver-derived plasma DNA molecules can be increased due to increased release of DNA molecules from the liver tissue as a result of tumor growth. In other cases, increased cell turnover, for example, as a result of organ transplant can also lead to increased plasma DNA released from the tissue with the transplant.

The methods provided herein can comprise determining the size of a tumor in the first tissue based on the absolute amount of the cell-free DNA molecules from the biological sample that are from the first tissue of the organism. A predetermined comparison chart, in which the amount of target cell-free DNA molecule and the tumor size are correlated, can be used for the tumor size determination. The detection of the tumor size can aid diagnosis, monitoring, and prognostication of the cancer.

The methods provided herein can comprise determining whether the cancer has metastasized to the first tissue based on the absolute amount of the cell-free DNA molecules from the biological sample that are from the first tissue of the organism. The absolute amount of target DNA molecules determined by the methods provided herein can provide a desirable differentiation between cancer patients with and without metastasis, as compared to fractional amount of the target DNA molecules.

Cancer types that the methods, compositions, and systems provided herein can be applicable to can comprise bladder cancer, bone cancer, a brain tumor, breast cancer, carcinoma of cervix, colorectal cancer, esophageal cancer, gastrointestinal cancer, hematopoietic malignancy, head and neck squamous cell carcinoma, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, or thyroid cancer. The metastatic tissue to be assessed by the methods provided herein can comprise bladder, bone, brain, breast, cervix, colon, esophagus, gastrointestinal tract, blood, head, neck, liver, lung, lymph node, nose, nasopharynx, mouth, oropharynx, ovary, prostate, skin, stomach, or thyroid.

As one skilled in the art would readily appreciate, cancer cells can spread locally by moving into nearby normal tissue, can spread regionally, to nearby lymph nodes, tissues, or organs, and can spread to distant parts of the body. The spread of a cancer from an initial first tissue to a second tissue can be called metastasis, and such a cancer can thus be called metastatic cancer. Exemplary types of cancer metastasis that the methods, compositions, and systems provided herein can be applied to can include metastasis taking place in the sites listed in Table 1.

TABLE 1

Exemplary Cancer Metastasis Sites

| Cancer Type | Metastasis Sites |
| --- | --- |
| Bladder | Bone, liver, lung |
| Breast | Bone, brain, liver, lung |
| Colon | Liver, lung, peritoneum |
| Kidney | Adrenal gland, bone, brain, liver, lung |
| Lung | Adrenal gland, bone, brain, liver, other lung |
| Melanoma | Bone, brain, liver, lung, skin, muscle |
| Ovary | Liver, lung, peritoneum |
| Pancreas | Liver, lung, peritoneum |
| Prostate | Adrenal gland, bone, liver, lung |
| Rectal | Liver, lung, peritoneum |
| Stomach | Liver, lung, peritoneum |
| Thyroid | Bone, liver, lung |
| Uterus | Bone, liver, lung, peritoneum, vagina |

In some cases, the methods, compositions, and systems as provided herein can be applied to diagnose, monitor, and prognosticate cancer when combined with other techniques that are available to one skilled in the art. In some cases, detection of other molecular markers, e.g., in nucleic acid, e.g., DNA, RNA, such as, copy number aberrations (CNAs), single nucleotide polymorphisms (SNPs), genetic mutations, germline mutations, somatic mutations, nucleic acids from a pathogen, e.g., a virus, e.g., an Epstein-Barr virus, size of cell-free nucleic acids, and fragmentation patterns of cell-free nucleic acids, can also be applied in combination with the methods, compositions, and systems as provided herein. The combination of techniques can help facilitate the detection of level of cancer, including, but not limited to, whether cancer exists, a stage of a cancer, a size of tumor, how many deletions or amplifications of a chromosomal region are involved (e.g. duplicated or tripled), and/or other measure of a severity of a cancer. The level of cancer can be a number of other characters. The level can be zero. The level of cancer can also include premalignant or precancerous conditions associated with deletions or amplifications.

In some cases, detection of copy number aberrations (CNAs), such as the methods disclosed in U.S. Pat. No. 8,741,811, can be used in combination with the methods provided herein. As discussed above, in some cases, based on absolute amount of cell-free nucleic acid from a first tissue, the methods provided herein can determine whether a cancer has metastasized into the first tissue. Detection of CNAs, on the other hand, can aid in identifying the origin of the metastatic cancer cells in the first tissue. In some cases, analysis of fragmentation pattern of cell-free nucleic acids, such as the methods disclosed in U.S. patent application Ser. No. 15/218,497, can be used in combination with the methods, compositions, and systems provided herein. In some cases, the subject methods, compositions, and systems can be used for detecting, monitoring, or prognosticating cancer in a subject in combination with any available approaches. Besides the aforementioned detection methods, one can also perform any appropriate tests like tumor biomarker tests (e.g., alpha-fetoprotein (AFP) for liver cancer, ALK gene for non-small-cell lung cancer, prostate-specific antigen (PSA) for prostate cancer, and thyroglobulin for thyroid cancer), physical examination, radiographic imaging (e.g., computed tomography scan, magnetic resonance imaging, Positron Emission Tomography (PET)), ultra sound examination, endoscopic examinations, biopsy, or cytology tests.

In some cases, the subject methods, compositions, or systems can be used for monitoring cancer in a subject on a regular, semi-regular, or non-regular schedule. For instance, a subject can take a cancer monitoring examination that makes use of the subject methods, compositions, or systems on a weekly, monthly, quarterly, or annually basis. In some cases, as subject can take such examinations about every 1, 2, 3, 4, 5, 6, 7, 8, 9, 10, 11, or more than 12 months. In some cases, the interval between two consecutive examinations can be determined based on the results of the most recent examination, e.g., in some cases, according to a physician's prescription or medical advice.

IV. Methods of Assessing Organ Transplant

Provided herein are methods of assessing organ transplant based on determination of an absolute amount of cell-free DNA molecules that are from the transplanted tissue. The transplanted tissues as described herein are considered as a tissue of the subject of concern.

The method as provided herein can take advantage of the correlation between the amount of cell-free DNA molecules that are from the transplanted tissue and the cell turnover rate in the transplanted tissue. The cell turnover rate can thereby be used as a criterion for assessing the organ transplant.

V. Composition for Analyzing Cell-Free DNA Molecules from a Tissue

Also provided herein are compositions for analyzing cell-free DNA molecules from a specific tissue, e.g. bone, liver, lung, brain, peritoneum, adrenal gland, skin, muscle, vagina, colon, bladder, breast, kidney, melanoma, ovary, pancreas, prostate, rectal, stomach, thyroid, or uterus.

A composition for determining amount of cell-free DNA molecules from a biological sample that are from liver of an organism can comprise a pair of primers for amplification of a liver-specific marker based on methylation status of the liver-specific marker. The liver-specific marker can comprise a polynucleotide sequence having at least 60%, 70%, 80%, 90%, 95%, 98%, or 99% identity to SEQ ID NO: 1. In some cases, the pair of primers comprises a primer comprising SEQ ID NO: 2, and a primer comprising SEQ ID NO: 3. In some cases, the composition further comprises a detectably-labeled probe comprising SEQ ID NO: 4 for detection of the liver-specific marker. In some cases, the composition further comprises a primer comprising SEQ ID NO: 5 and a primer comprising SEQ ID NO: 6. In some cases, the composition further comprises a detectably-labeled probe comprising SEQ ID NO: 7 for detection of the liver-specific marker.

A composition provided herein can comprise a pair of primers for amplification of a liver-specific marker based on methylation status of the colon-specific marker. The colon-specific marker can comprise a polynucleotide sequence having at least 60%, 70%, 80%, 90%, 95%, 98%, or 99% identity to SEQ ID NO: 8. In some cases, the pair of primers comprises a primer comprising SEQ ID NO: 9, and a primer comprising SEQ ID NO: 10. In some cases, the composition further comprises a detectably-labeled probe comprising SEQ ID NO: 11 for detection of the colon-specific marker. In some cases, the composition further comprises a primer comprising SEQ ID NO: 12 and a primer comprising SEQ ID NO: 13. In some cases, the composition further comprises a detectably-labeled probe comprising SEQ ID NO: 14 for detection of the colon-specific marker.

VI. Biological Sample

The biological sample used in methods provided herein can include any tissue or material derived from a living or dead subject. A biological sample can be a cell-free sample. A biological sample can comprise a nucleic acid (e.g., DNA, e.g., genomic DNA or mitochondrial DNA, or RNA) or a fragment thereof. The nucleic acid in the sample can be a cell-free nucleic acid. A sample can be a liquid sample or a solid sample (e.g., a cell or tissue sample). The biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. Stool samples can also be used. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). The biological sample can be treated to physically disrupt tissue or cell structure (e.g., centrifugation and/or cell lysis), thus releasing intracellular components into a solution which can further contain enzymes, buffers, salts, detergents, and the like which are used to prepare the sample for analysis.

Methods, compositions, and systems provided herein can be used to analyze nucleic acid molecules in a biological sample. The nucleic acid molecules can be cellular nucleic acid molecules, cell-free nucleic acid molecules, or both. The cell-free nucleic acids used by methods as provided herein can be nucleic acid molecules outside of cells in a biological sample. The cell-free nucleic acid molecules can be present in various bodily fluids, e.g., blood, saliva, semen, and urine. Cell-free DNA molecules can be generated owing to cell death in various tissues that can be caused by health conditions and/or diseases, e.g., tumor invasion or growth, immunological rejection after organ transplantation.

Cell-free nucleic acid molecules, e.g., cell-free DNA, used in methods as provided herein can exist in plasma, urine, saliva, or serum. Cell-free DNA can occur naturally in the form of short fragments. Cell-free DNA fragmentation can refer to the process whereby high molecular weight DNA (such as DNA in the nucleus of a cell) are cleaved, broken, or digested to short fragments when cell-free DNA molecules are generated or released. Methods, compositions, and systems provided herein can be used to analyze cellular nucleic acid molecules in some cases, for instance, cellular DNA from a tumor tissue, or cellular DNA from white blood cells when the patient has leukemia, lymphoma, or myeloma. Sample taken from a tumor tissue can be subject to assays and analyses according to some examples of the present disclosure.

VII. Subjects

Methods, compositions, and systems provided herein can be used to analyze sample from a subject, e.g., organism, e.g., host organism. The subject can be any human patient, such as a cancer patient, a patient at risk for cancer, or a patient with a family or personal history of cancer. In some cases, the subject is in a particular stage of cancer treatment. In some cases, the subject can have or be suspected of having cancer. In some cases, whether the subject has cancer is unknown.

A subject can have any type of cancer or tumor. In an example, a subject can have colon cancer, or cancer of the large intestine. In another example, a subject can have colorectal cancer, or cancer of the colon and rectum. In another example, a subject can have liver cancer, e.g., hepatocellular carcinoma. Non-limiting examples of cancer can include, but are not limited to, adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, hepatocellular carcinoma, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The lymphoma can be any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The leukemia can be any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, the patient can have a cancer that is not breast cancer.

Examples of cancer include cancers that cause solid tumors as well as cancers that do not cause solid tumors. Furthermore, any of the cancers mentioned herein can be a primary cancer (e.g., a cancer that is named after the part of the body where it first started to grow) or a secondary or metastatic cancer (e.g., a cancer that has originated from another part of the body).

A subject diagnosed by any of the methods described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of patients that can benefit can be patients over the age of 40. Another particular class of patients that can benefit can be pediatric patients. Furthermore, a subject diagnosed by any of the methods or compositions described herein can be male or female.

Any of the methods disclosed herein can also be performed on a non-human subject, such as a laboratory or farm animal, or a cellular sample derived from an organism disclosed herein. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

As discussed above, the subject methods, compositions, and kits can be used on subjects in various stages of cancer treatment. Results from analyses of cell-free nucleic acids in biological samples of a subject using the subject methods, compositions, and kits can be used for guiding treatment plans for the subject. In some cases, medication or therapies to treat or cure cancer in the subject can be needed. Exemplary treatment options can include chemotherapy, radiation therapy, surgical removal of tumor tissues, immunotherapy, targeted therapy, hormone therapy, and stem cell therapy. In some cases, guidance can be provided as to the choice of the different types of treatment options. In some non-limiting examples, a patient can have finished treatment of a first cancer, e.g., surgical removal of tumor tissue in affected liver leaves, and the patient can be subject to routine monitoring tests using the subject methods, compositions, or kits, in order to examine whether or not there is recurrence of the liver cancer or metastasis. In these cases, the test results can be used to provide guidance as to whether or not the patient would need further treatment of the cancer, and if recurrence of the liver cancer or metastasis into other tissue happens, what treatment options can be applied. In some cases, guidance can be provided as to the specific dosage or administration regimen of the treatment. For instance, the amount of cell-free nucleic acids from a certain tissue can be correlated with the dosage of medication that is to be administered to the patient, or with the frequency/interval of drug administration (e.g., daily, weekly, bi-weekly, or monthly). In some cases, the results from last analysis can be used as basis for evaluating and designing the treatment options and follow-on monitoring analysis.

VIII. Computer System

Any of the methods disclosed herein can be performed and/or controlled by one or more computer systems. In some examples, any step of the methods disclosed herein can be wholly, individually, or sequentially performed and/or controlled by one or more computer systems. Any of the computer systems mentioned herein can utilize any suitable number of subsystems. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems can be interconnected via a system bus. Additional subsystems include a printer, keyboard, storage device(s), and monitor that is coupled to display adapter. Peripherals and input/output (I/O) devices, which couple to I/O controller, can be connected to the computer system by any number of connections known in the art such as an input/output (I/O) port (e.g., USB, FireWire®). For example, an I/O port or external interface (e.g., Ethernet, Wi-Fi, etc.) can be used to connect computer system to a wide area network such as the Internet, a mouse input device, or a scanner. The interconnection via system bus allows the central processor to communicate with each subsystem and to control the execution of a plurality of instructions from system memory or the storage device(s) (e.g., a fixed disk, such as a hard drive, or optical disk), as well as the exchange of information between subsystems. The system memory and/or the storage device(s) can embody a computer readable medium. Another subsystem is a data collection device, such as a camera, microphone, accelerometer, and the like. Any of the data mentioned herein can be output from one component to another component and can be output to the user.

A computer system can include a plurality of the same components or subsystems, e.g., connected together by external interface or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Figure 10:
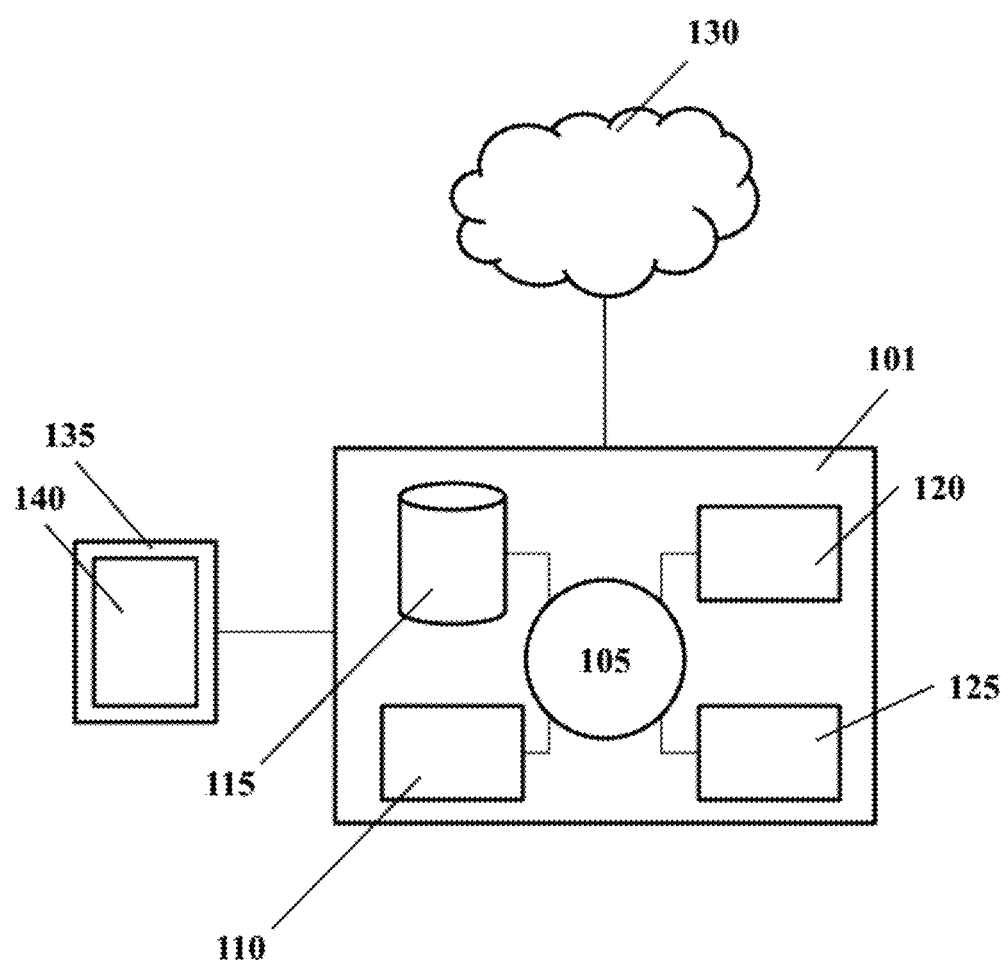
FIG. 10 shows a computer control system that can be programmed or otherwise configured to implement methods provided herein.

The present disclosure provides computer control systems that are programmed to implement methods of the disclosure. FIG. 10 shows a computer system 101 that is programmed or otherwise configured to determine an absolute amount of cell-free nucleic acid molecules from a tissue of an organism as described herein. The computer system 101 can implement and/or regulate various aspects of the methods provided in the present disclosure, such as, for example, controlling sequencing of the nucleic acid molecules from a biological sample, performing various steps of the bioinformatics analyses of sequencing data as described herein, integrating data collection, analysis and result reporting, and data management. The computer system 101 can be an electronic device of a user or a computer system that is remotely located with respect to the electronic device. The electronic device can be a mobile electronic device.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the computer system 101, can implement a peer-to-peer network, which can enable devices coupled to the computer system 101 to behave as a client or a server.

The CPU 105 can execute a sequence of machine-readable instructions, which can be embodied in a program or software. The instructions can be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some cases, the circuit is an application specific integrated circuit (ASIC).

The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user (e.g., a Smart phone installed with application that receives and displays results of sample analysis sent from the computer system 101). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 101, can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, can take many forms, including but not limited to, a tangible storage medium, a carrier wave medium or physical transmission medium. Non-volatile storage media include, for example, optical or magnetic disks, such as any of the storage devices in any computer(s) or the like, such as can be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 101 can include or be in communication with an electronic display 135 that comprises a user interface (UI) 140 for providing, for example, results of sample analysis, such as, but not limited to graphic showings of relative and/or absolute amounts of cell-free nucleic acids from different tissues, control or reference amount of cell-free nucleic acids from certain tissues, comparison between detected and reference amounts, and readout of presence or absence of cancer metastasis. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 105. The algorithm can, for example, control sequencing of the nucleic acid molecules from a sample, direct collection of sequencing data, analyzing the sequencing data, or determining a classification of pathology based on the analyses of the sequencing data.

Figure 11:
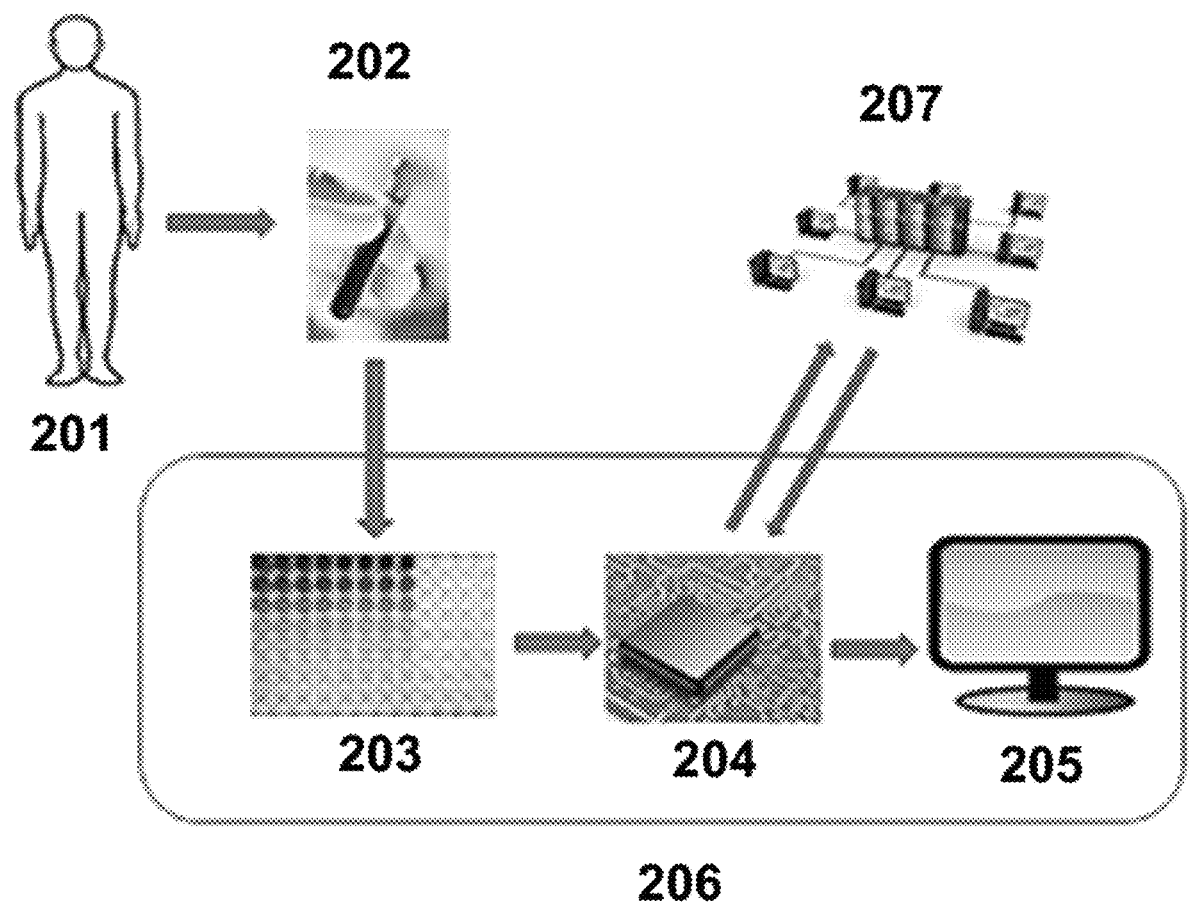
FIG. 11 shows a diagram of the methods and systems as disclosed herein.

In some cases, as shown in FIG. 11, a sample 202 can be obtained from a subject 201, such as a human subject. A sample 202 can be subjected to one or more methods as described herein, such as performing an assay. In some cases, an assay can comprise hybridization, amplification, sequencing, labeling, epigenetically modifying a base, or any combination thereof. One or more results from a method can be input into a processor 204. One or more input parameters such as sample identification, subject identification, sample type, a reference, or other information can be input into a processor 204. One or more metrics from an assay can be input into a processor 204 such that the processor can produce a result, such as a classification of pathology (e.g., diagnosis) or a recommendation for a treatment. A processor can send a result, an input parameter, a metric, a reference, or any combination thereof to a display 205, such as a visual display or graphical user interface. A processor 204 can (i) send a result, an input parameter, a metric, or any combination thereof to a server 207, (ii) receive a result, an input parameter, a metric, or any combination thereof from a server 207, (iii) or a combination thereof.

Aspects of the present disclosure can be implemented in the form of control logic using hardware (e.g., an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application can be implemented as software code to be executed by a processor using any suitable computer language such as, for example, Java, C, C++, C#, Objective-C, Swift, or scripting language such as Perl or Python using, for example, conventional or object-oriented techniques. The software code can be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium can be any combination of such storage or transmission devices.

Such programs can also be encoded and transmitted using carrier signals adapted for transmission via wired, optical, and/or wireless networks conforming to a variety of protocols, including the Internet. As such, a computer readable medium can be created using a data signal encoded with such programs. Computer readable media encoded with the program code can be packaged with a compatible device or provided separately from other devices (e.g., via Internet download). Any such computer readable medium can reside on or within a single computer product (e.g., a hard drive, a CD, or an entire computer system), and can be present on or within different computer products within a system or network. A computer system can include a monitor, printer, or other suitable display for providing any of the results mentioned herein to a user.

Any of the methods described herein can be totally or partially performed with a computer system including one or more processors, which can be configured to perform the steps. Thus, embodiments can be directed to computer systems configured to perform the steps of any of the methods described herein, with different components performing a respective steps or a respective group of steps. Although presented as numbered steps, steps of methods herein can be performed at a same time or in a different order. Additionally, portions of these steps can be used with portions of other steps from other methods. Also, all or portions of a step can be optional. Additionally, any of the steps of any of the methods can be performed with modules, units, circuits, or other approaches for performing these steps.

EXAMPLES

The examples below further illustrate the described embodiments without limiting the scope of this disclosure.

Example 1. Materials and Methods

This example describes several methods utilized for Examples 2-5.

Subjects

Patients who previously underwent liver transplantation were recruited during their visits to the liver transplantation clinic from the Department of Surgery of the Prince of Wales Hospital in Hong Kong. Patients with chronic hepatitis B virus (HBV) infection and cirrhosis were recruited from the Department of Medicine and Therapeutics of the Prince of Wales Hospital in Hong Kong. Patients with hepatocellular carcinoma (HCC) and CRC were recruited from the Department of Surgery and the Department of Clinical Oncology of the Prince of Wales Hospital in Hong Kong. The demographics of the recruited subjects are shown in the Table 2. All recruited subjects gave written consents. The study was approved by the Joint Hospital Authority New Territories East Cluster—The Chinese University of Hong Kong Clinical Research Ethics Committee.

TABLE 2

Demographics of subjects analyzed in the study.

| Health and disease status | Number | Sex (M:F) | Age median (range) |
| --- | --- | --- | --- |
| Healthy subjects | 30 | 16:14 | 57 (26-73) |
| Liver transplant recipients | 13 | 12:1 | 67 (54-73) |
| HCC patients | 40 | 36:4 | 60 (39-82) |
| HBV carriers | 20 | 20:0 | 52 (43-77) |
| Cirrhosis patients | 9 | 9:0 | 62 (53-75) |
| CRC patients with liver metastasis | 27 | 20:7 | 62 (34-78) |
| CRC patients without liver metastasis | 35 | 18:17 | 67 (51-83) |

Sample Preparation

For each subject, 10 mL peripheral blood was collected into EDTA-containing tubes. The blood sample was processed within 6 h after blood withdrawal for the separation of plasma and buffy coat. DNA was extracted from plasma using the QIAamp DSP DNA Mini Kit (Qiagen) following the manufacturer's protocol. The DNA extracted from 2 to 4 mL of plasma was subjected to two rounds of bisulfite treatment using an Epitect Plus Bisulfite Kit (Qiagen). The bisulfite converted DNA was eluted in 50 µL of water for downstream analysis.

Identification of Liver-Specific and Colon-Specific Methylation Markers

The methylation profiles of the tissue of interest (i.e. the liver or the colon) were compared with those of other blood cells and tissues to mine a tissue-specific methylation marker. The methylation profiles of different cell types were retrieved from the database of the RoadMap Epigenomics Project for the lung, esophagus, small intestines, colon, pancreas, urinary bladder, heart, and liver, and the database of the BLUEPRINT project for erythroblasts, neutrophils, B-lymphocytes and T-lymphocytes.

The following criteria for a methylation marker were established.

1. A CpG site was defined as hypermethylated in a target tissue (i.e. liver or colon) if the methylation density of the CpG site was >50% in the target tissue and <20% in other blood cells and tissues.

2. A stretch of at least 5 hypermethylated CpG sites would be within the differentiated methylated region (DMR) so as to improve the latter's signal-to-noise ratio and analytical specificity of the methylation marker.

3. The DMR should be shorter than 166 bp because most of the circulating DNA molecules are short fragments and the peak size is 166 bp.

DMRs for the Liver and Colon

Figure 7:
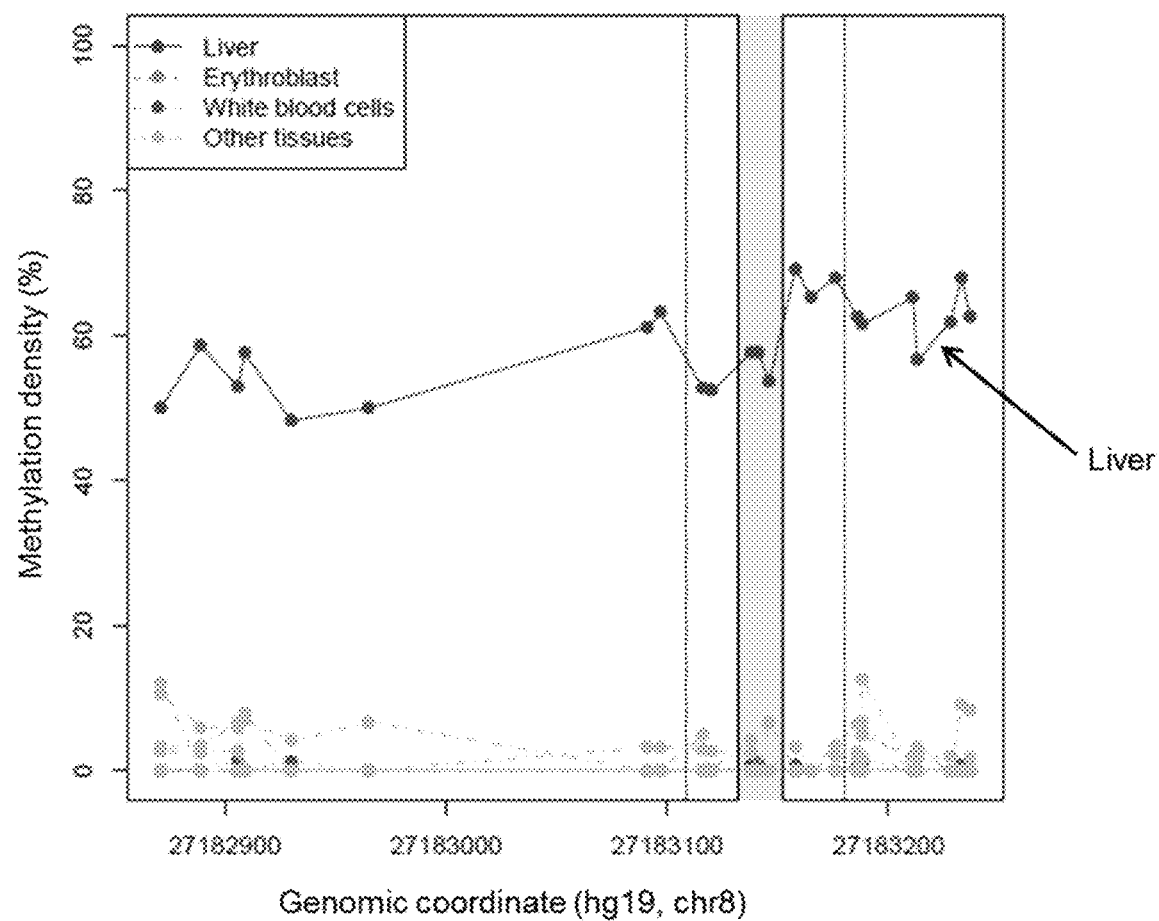
FIG. 7 shows the methylation densities of the CpG sites within the protein tyrosine kinase 2 beta (PTK2B) gene region.
Figure 8:
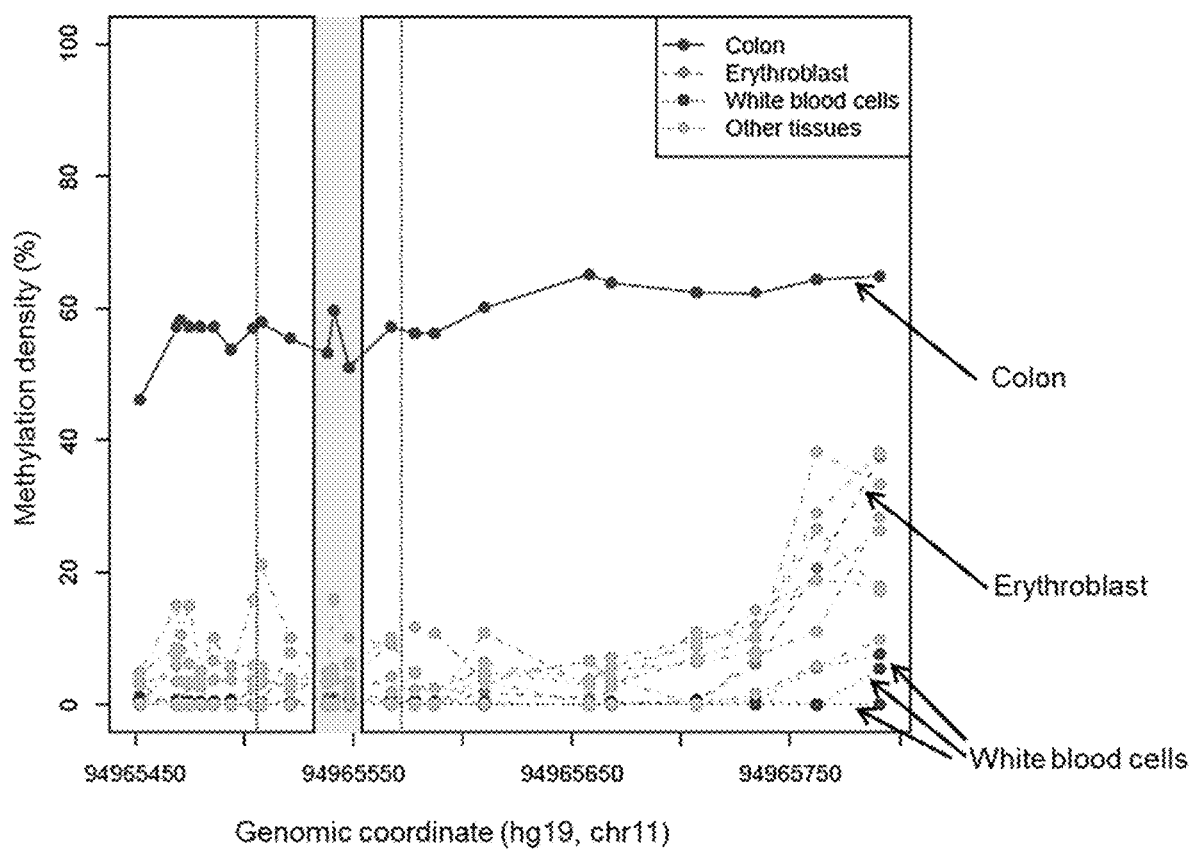
FIG. 8 shows the methylation densities of the CpG sites within the Sestrin 3 (SESN3) gene region.

Using the criteria above, one liver-specific marker and one colon-specific marker were identified. The liver-specific DMR was located in the exonic region of the protein tyrosine kinase 2 beta (PTK2B) gene on chromosome 8. The eight CpG sites within the liver-specific DMR were hypermethylated in the liver but hypomethylated in other tissues and blood cells (FIG. 7). The PTK2B gene is located on chromosome 8 and the genomic coordinates of the CpG sites are shown on the X-axis of FIG. 7. All the eight CpG sites located within the DMR (region between the two vertical dotted lines) are hypermethylated for the liver compared with other tissues. The region highlighted in yellow contains three CpG sites within the fluorescent probes of the digital PCR assays (see Table 3). The other CpG sites on each side of the highlighted region within the DMR were covered by the primers of the digital PCR assays. The colon-specific DMR was within the exonic region of the Sestrin 3 (SESN3)

gene on chromosome 11. All the six CpG sites within the colon-specific DMR were hypermethylated in colon tissues (FIG. 8) but hypomethylated in other tissues. The SESN3 is located on chromosome 11 and the genomic coordinates of the CpG sites are shown on the X-axis in FIG. 8. All the six CpG sites located within the DMR (region between the two vertical dotted lines) are hypermethylated for the colon compared with other tissues. The three CpG sites located within the region highlighted in yellow were covered by the fluorescent probes of the colon-specific methylation assay (see Table 3). The other CpG sites on each side of the highlighted region within the DMR were covered by the primers of the digital PCR assays. For illustration purpose, individual results in FIGS. 7 and 8 for liver, urinary bladder, esophagus, heart, lung, pancreas, and small intestines are not shown, their mean values are represented by "Other tissues".

Droplet Digital PCR Design and Performance

Two droplet digital PCR assays were developed to quantify the methylated and unmethylated DNA molecules in each of liver-specific and colon-specific methylation markers. The sequences of primers and probes for the assays are listed in the Table 3 (The underlined nucleotides in the primers and probes were the differentially methylated cytosines at the CpG sites). The two droplet digital PCR assays can quantify methylated (from target tissue) and unmethylated (from non-target tissue) using probes labeled with FAM and VIC, respectively. The liver-specific marker was PTK2B gene marker site (chr8: 27,183,116-27,183,176), and the colon-specific marker was SESN3 gene marker site (chr11: 94,965,508-94,965,567).

For each sample, digital PCR analysis was run in duplicates. A total volume of 20 μL of reaction mix was prepared, containing 8 μL of bisulfite converted DNA, a final concentration of 450 nM of each of forward primers and reverse primers, 250 nM of unmethylation-specific probe, and 350 nM (liver assay) or 250 nM (colon assay) of methylation-specific probe for the colon assay. The reaction mix was submitted to droplets generation before the PCR reaction using the BioRad QX200 ddPCR droplet generator. Universally methylated DNA (CpGenome Human Methylated DNA from EMD Millipore) and universally unmethylated DNA (EpiTect Unmethylated Human Control DNA from Qiagen) were run on each plate as positive and negative controls. The thermal profile was: 95° C. for 10 minutes followed by 45 cycles of 94° C. for 15 seconds and 60° C. (liver assay) or 56° C. (colon assay) for 1 minute and a final incubation at 98° C. for 10 minutes. After the PCR, droplets from each sample were analyzed by the QX200 droplet reader and the results were interpreted using the QuantaSoft (version 1.7) software. The cut-off values for positive fluorescence signals were determined with reference to the controls. The numbers of methylated and unmethylated DNA sequences in each sample was calculated using combined counts from duplicate wells followed by Poisson correction. The calculation of the concentration of the methylated or unmethylated DNA sequences in plasma is as follows:

$$Cr = -\ln\left(1 - \frac{P}{R}\right) \times \left(\frac{Ve}{Vd}\right)$$

where Cr represents the concentration of the target molecules in plasma (i.e. the methylated or unmethylated DNA sequences), P represents the number of droplets containing amplified signal for the targeted molecules (either the methylated or unmethylated DNA sequences), R represents the number of total droplets analyzed (with and without amplified signals), $V_d$ represents the mean volume of a droplet (i.e. $0.9 \times 10^{-3}$ μL in the current example) and Ve represents the volume of plasma used for the experiment (i.e. 320 μL in the current example).

TABLE 3

Oligonucleotide sequences for the digital PCR assays

| Primers/probes/marker | Sequence (5'-3') | SEQ ID NO |
|---|---|---|
| PTK2B gene marker site | CGGCCGACTTACCTGTACTTGCCGCCGTCCCGGCTCACCTGGCG GTGCCCGAGGAGTAGTC | 1 |
| Methylated assay (for liver-derived DNA) | | |
| Forward primer (F1) | TTTATTTGTTCGGTCGATTTATTTGTA | 2 |
| Reverse primer (R1) | AACGACTACTCCTCGAACACCG | 3 |
| Fluorescence probe (P1) | 5'-FAM-TTGTCGTCGTTTCGGTT-MGB-3' | 15 |
| Fluorescence probe (P1) sequence | TTGTCGTCGTTTCGGTT | 4 |
| Unmethylated assay (for non-liver-derived DNA) | | |
| Forward primer (F2) | TGTATATTTATTTGTTTGGTTGATTTATTTGTA | 5 |
| Reverse primer (R2) | CCAACAACTACTCCTCAAACACCA | 6 |
| Fluorescence probe (P2) | 5'-VIC-TTTGTTGTTGTTTTGGTTTA-MGB-3' | 16 |

TABLE 3-continued

Oligonucleotide sequences for the digital PCR assays

| Primers/probes/marker | Sequence (5'-3') | SEQ ID NO |
|---|---|---|
| Fluorescence probe (P2) sequence | TTTGTTGTTGTTTTGGTTTA | 7 |
| SESN3 gene marker site | CGCAACCTGCTCCCGAGTGAGAACAAAGGCCGGCGCAGAGCGAGAACCTGATTGGTGCCC | 8 |
| Methylated assay (for colon-derived DNA) | | |
| Forward primer (F1) | CGTAATTTGTTTTCGAGTGAGAATAA | 9 |
| Reverse primer (R1) | AAAAACCGAACACCAATCAAATTC | 10 |
| Fluorescence probe (P1) | 5'-FAM-TCGGCGTAGAGCGA-MGB-3' | 17 |
| Fluorescence probe (P1) sequence | TCGGCGTAGAGCGA | 11 |
| Unmethylated assay (for non-colon-derived DNA) | | |
| Forward primer (F2) | GTTTGTAATTTGTTTTTGAGTGAGAATAA | 12 |
| Reverse primer (R2) | AAAAACCAAACACCAATCAAATTC | 13 |
| Fluorescence probe (P2) | 5'-VIC-AGGTTGGTGTAGAGTGA-MGB-3' | 18 |
| Fluorescence probe (P2) sequence | AGGTTGGTGTAGAGTGA | 14 |

Analysis of DNA from Different Types of Samples

Formalin-fixed paraffin embedded (FFPE) samples of 10 types of tissue (e.g. liver, lung, esophagus, stomach, small intestines, colon, pancreas, urinary bladder, heart, and brain) were retrieved from the Department of Anatomical and Cellular Pathology of the Prince of Wales Hospital in Hong Kong. These tissues were confirmed to be normal on histological examination. Buffy coat samples were collected from healthy subjects. DNA was extracted from FFPE tissues using a QIAamp DNA Mini Kit (Qiagen). DNA from buffy coat was extracted using the QIAamp DNA Blood Mini Kit (Qiagen). Bisulfite conversion was performed using 1 μg of cellular DNA. The converted DNA was eluted in 20 μL water and then diluted 50 fold for downstream analysis.

Measurement of Donor-Derived DNA in Plasma of Liver Transplant Recipients

DNA extracted from the liver tissue of donors and the buffy coat of recipients was analyzed to determine genotype information of donors and recipients using the Illumina iScan system. DNA extracted from 4 mL of plasma for each recipient was used for sequencing library preparation. Plasma DNA sequencing libraries were prepared with a KAPA Library Preparation Kit (KAPA Biosystems) following the manufacturer's instructions. The indexed libraries were then multiplexed and sequenced using the Illumina HiSeq 2500 platform (75×2 cycles). At least 20 million paired-end reads were obtained for each sample. Paired-end reads were aligned to the non-repeat-masked human reference genome (GRCh 37/hg 19) using the Short Oligonucleotide Alignment Program 2 (SOAP2). Only paired-end reads with both ends aligned to the same chromosome with the correct orientation and aligned to a single location in the human genome were included. The paired-end reads spanning an insert size ≤600 bp were retrieved for analysis. If more than one pair of reads was mapped to the same genome location (i.e. duplicated reads), only one pair of reads was retained for subsequent analysis. Up to two nucleotide mismatches were allowed for either member of the paired-end reads. The fractional concentration of donor-specific DNA in the circulation was determined by counting sequencing reads with single nucleotide polymorphism (SNP) alleles that were homozygous in the recipient and heterozygous in the donor.

Example 2. Tissue-Specificity of the Liver and Colon Markers

For both the liver-specific and colon-specific markers, the DNA molecules derived from the target tissue would be hypermethylated and those from the non-target tissue would be hypomethylated. Therefore, the percentage of total molecules was denoted being methylated in the liver assay as L % and the percentage of total molecules was denoted being methylated in the colon assay as C %. To confirm the specificity of the liver and colon markers, the DNA extracted from buffy coat samples and 10 types of normal tissues were analyzed using these two digital PCR assay sets. For each type of tissue, 4 samples from different individuals were included.

The mean L % for the liver tissues was 67% (range: 57%-76%) and the mean L % for other tissue types were 0.6% (range: 0.0%-2.2%). The results for each tissue type are summarized in the Table 4. These results suggested that the liver assay was able to specifically detect liver-derived DNA.

TABLE 4

Mean fractional concentration of liver-derived DNA (L %) and colon-derived DNA (C %)

| Tissue | Mean L % | Mean C % |
|---|---|---|
| Liver | 67 | 0.8 |
| Colon | 0.4 | 22 |
| Brain | 1.9 | 0.8 |
| Esophagus | 0.3 | 1.4 |
| Heart | 0.6 | 0.2 |
| Lung | 0.3 | 1.4 |
| Pancreas | 0.3 | 0.9 |
| Small bowel | 0.3 | 4.1 |
| Stomach | 0.1 | 1.3 |
| Urinary bladder | 2.2 | 1.3 |
| Buffy coat | 0.0 | 0.1 |

The mean C % of colon tissues were 22% (range: 17%-33%). The mean C % for all other tissues was 1.2% (range: 0.1%-4.1%) indicating the specificity of the methylated sequences as being colon derived. The relatively low C % in colon tissues was probably due to the non-homogenous cellular compositions of the colon tissues. This relatively low C % in colon tissues would not significantly hamper its clinical application when the same assay would be used for comparing the levels of subjects with different disease status.

Figure 2:
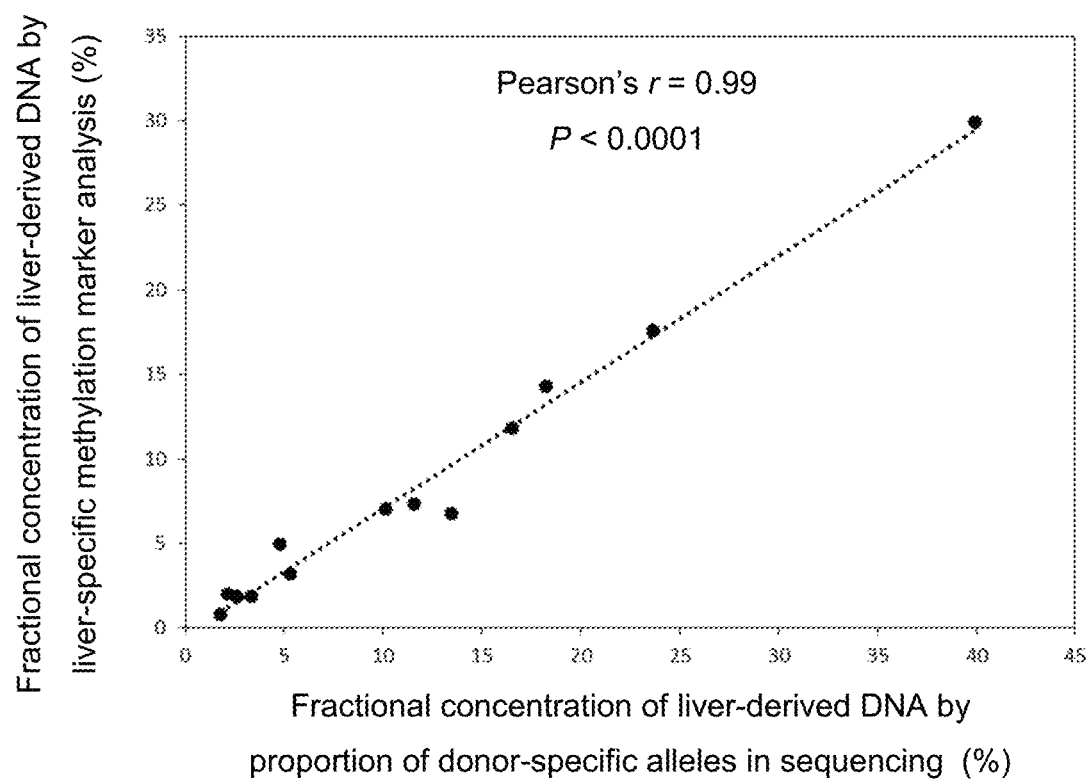
FIG. 2 shows correlation between fractional concentrations of liver-derived DNA in the plasma of liver transplant recipients based on liver-specific methylation marker analysis (droplet digital PCR) and donor-specific alleles analysis by sequencing.

Example 3. Plasma Concentrations of Liver-Derived DNA in Liver Transplant Recipients The quantitative accuracy of the liver-specific assay was validated through the analysis of the plasma of liver transplant recipients. In these subjects, the fractional concentrations of DNA derived from the transplanted liver could be accurately determined from the proportion of plasma DNA molecules carrying the donor-specific alleles using next-generation sequencing. 14 plasma samples collected from 13 patients who had received liver transplants were analyzed by both the liver-specific methylation marker and sequencing. A positive linear relationship was observed between the concentrations determined by these two methods (R=0.99, P<0.0001, Pearson correlation, FIG. 2) indicating that the liver-specific methylation marker can accurately reflect the concentration of liver-derived DNA in plasma.

As demonstrated here, the measurement of the percentage contribution of liver DNA concentration by the liver-specific methylation marker correlated well with the results based on the measurement of donor-specific alleles. These results confirmed the accuracy of the liver-specific marker in reflecting the concentration of liver-derived DNA in plasma.

Example 4. Increased Liver-Derived DNA in the Plasma of HCC Patients

The absolute and fractional concentrations of liver-derived DNA were determined by the digital PCR targeting the sequences with liver-specific methylation pattern in 40 HCC patients, 9 cirrhotic patients, 20 chronic HBV carriers and 30 healthy subjects.

Figure 3A:
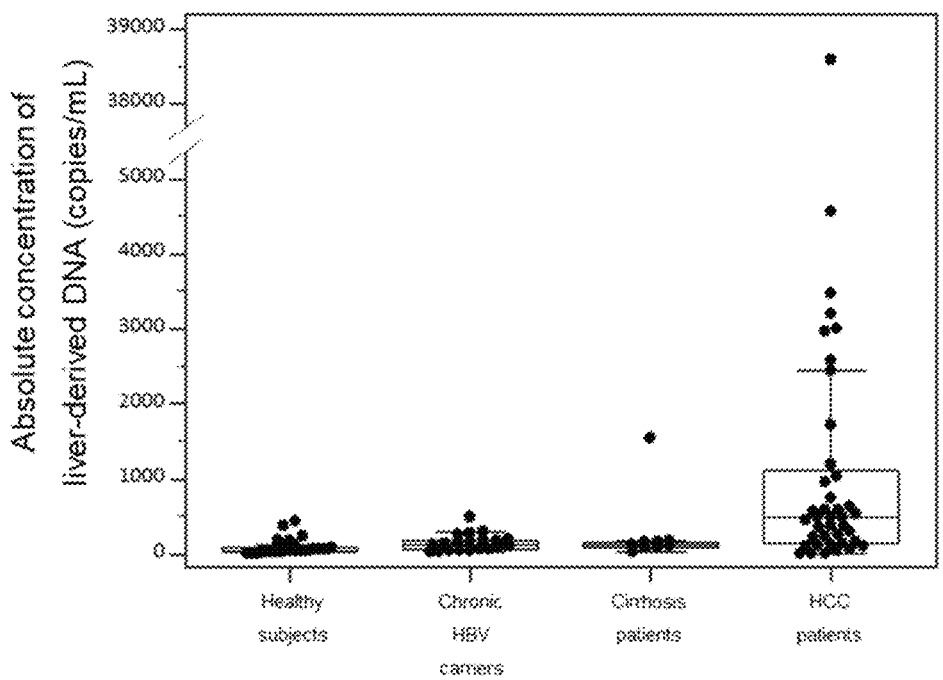
FIGS. 3A and 3B show absolute concentrations (FIG. 3A) and fractional concentrations (FIG. 3B) of liver-derived DNA using droplet digital PCR in the plasma of healthy subjects, chronic HBV carriers, cirrhotic patients and HCC patients.

The median concentration of liver-derived methylated sequences for the healthy subjects, chronic HBV carriers, cirrhotic patients and HCC patients were 40 copies/mL (interquartile range (IQR): 18-86), 122 copies/mL (IQR: 47-185), 118 copies/mL (IQR: 86-159), and 487 (IQR: 138-1151), respectively (FIG. 3A). The concentrations were significantly different across the four groups (P<0.001, Kruskal Wallis test). In the post-hoc analysis, the plasma concentrations of liver-derived DNA of the HCC patients were significantly higher than the healthy subjects (P<0.001, Dunn's test) and the chronic HBV carriers (P=0.015, Dunn's test) but not the cirrhotic patient groups (P=0.248, Dunn's test). The concentrations of the healthy subjects, chronic HBV carriers and cirrhotic patients were not statistically different (P>0.05, Dunn's test).

Figure 3B:
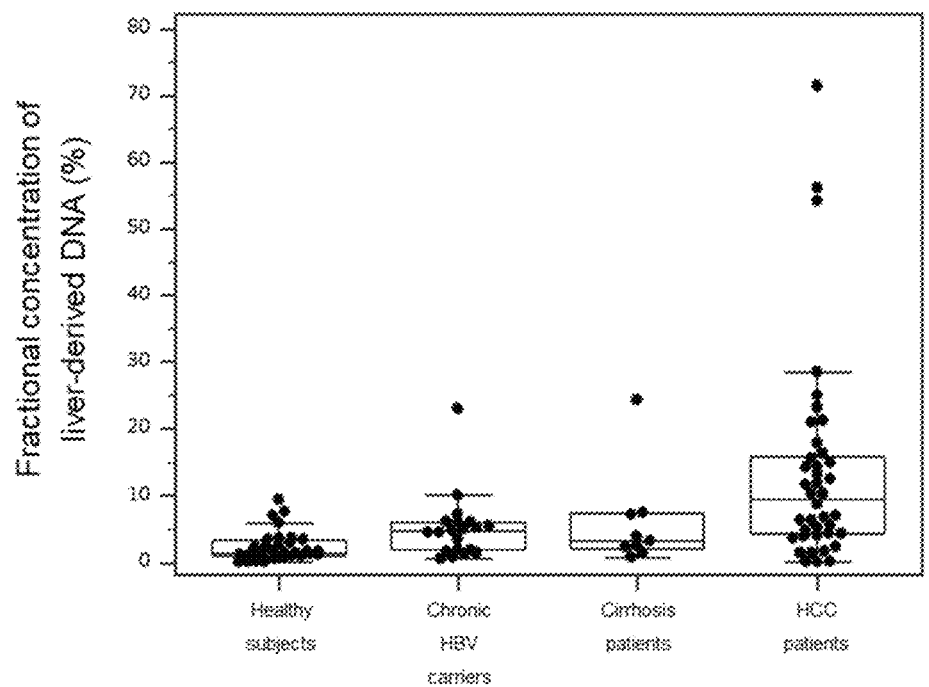

The median fractional concentrations of the liver-derived DNA in plasma for the healthy subjects, chronic HBV carriers, cirrhotic patients and HCC patients were 1.4% (IQR: 0.94%-3.2%), 4.6% (IQR: 1.7%-6.0%), 3.0% (interquartile range: 1.8%-7.3%) and 9.4% (IQR: 4.1%-16.0%), respectively (FIG. 3B). The fractional concentrations were significantly different across the four groups (P<0.001, Kruskal Wallis test). In the post-hoc analysis, the plasma concentrations of liver-derived DNA of the HCC patients were significantly higher than the healthy subjects (P<0.001, Dunn's test), but not the chronic HBV carriers (P=0.129, Dunn's test) and the cirrhotic patients (P=0.592, Dunn's test). The concentrations of the healthy subjects, chronic HBV carriers and cirrhotic patients were not statistically different.

Figure 9:
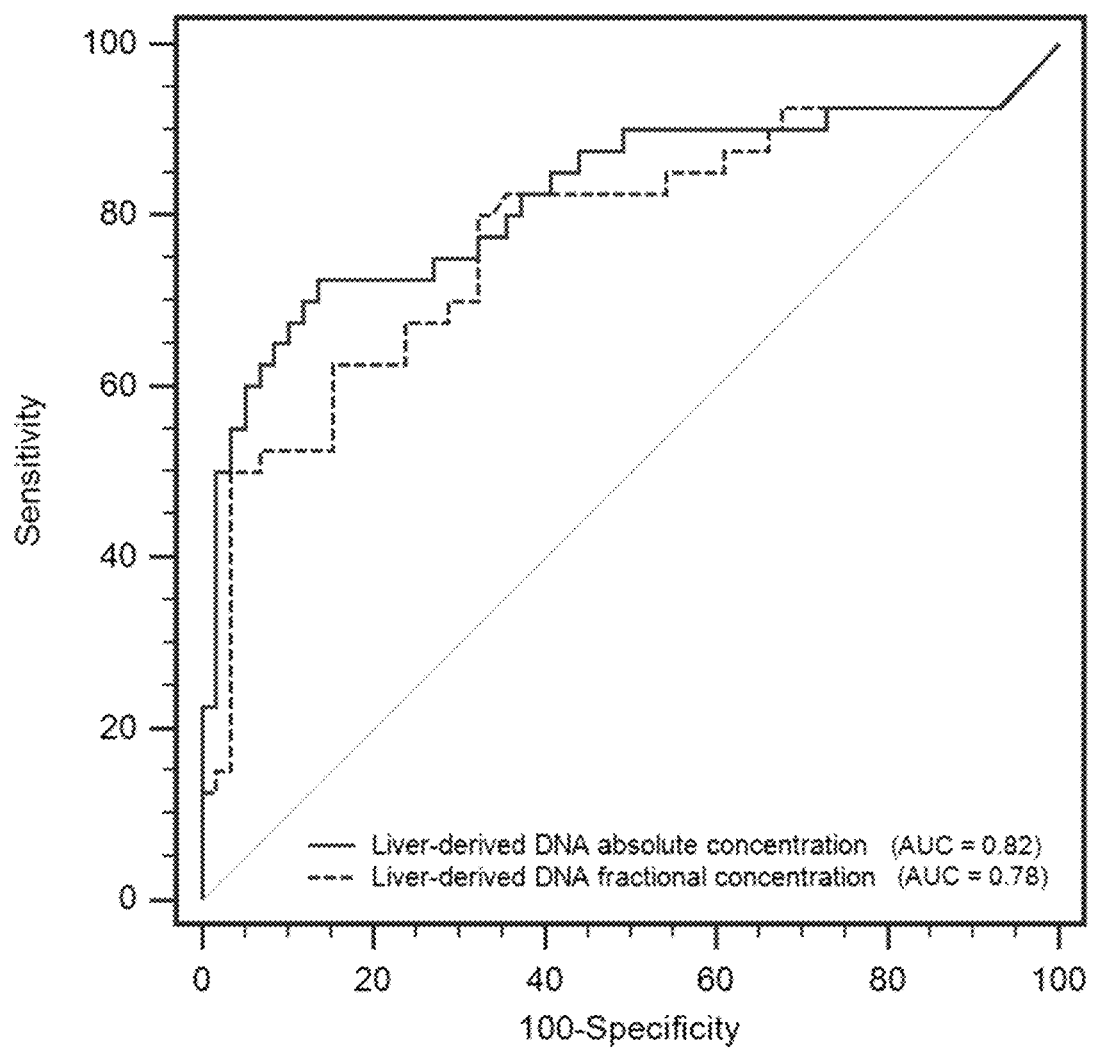
FIG. 9 shows a ROC curve for using the absolute and fractional concentrations of liver-derived DNA to differentiate HCC patients from non-HCC subjects.

These results demonstrated that the analysis of both the absolute and fractional concentrations of liver-derived DNA in plasma could differentiate HCC patients from non-HCC subjects (including healthy subjects, chronic HBV carriers and cirrhotic patients). To further determine if absolute or fractional concentration would be better for differentiating HCC and non-HCC subjects, receiver operating characteristic (ROC) curve analysis was performed (FIG. 9). The areas under curve (AUC) were 0.82 and 0.78, for absolute and fractional concentrations, respectively. The difference in the AUCs was statistically significant (P=0.022, Delong test).

Figure 4A:
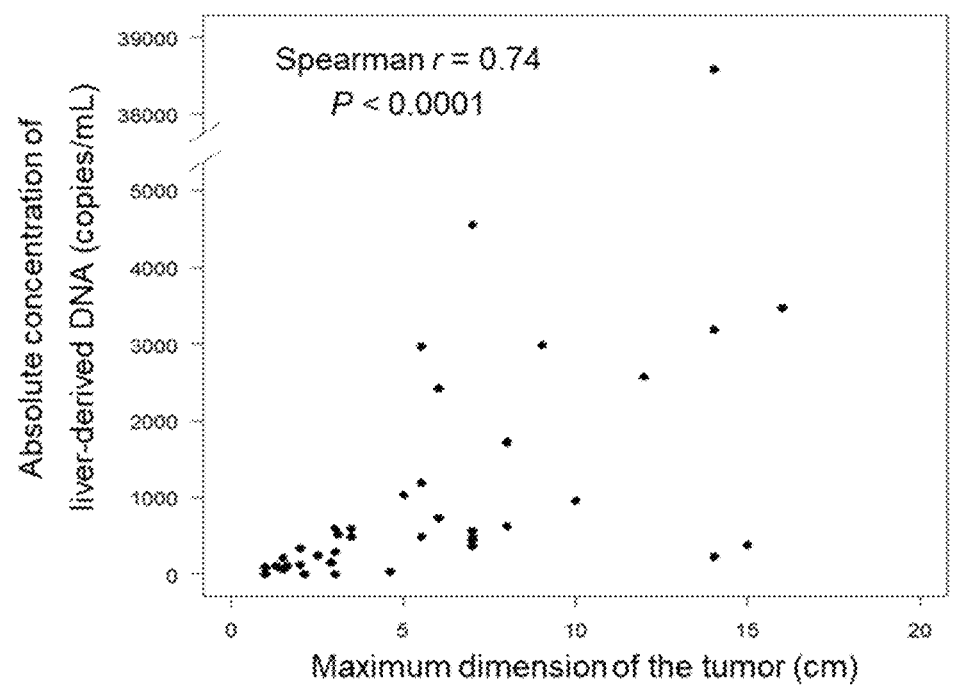
FIGS. 4A and 4B show correlation between the maximal dimension of the tumor and the absolute concentration (FIG. 4A) and the fractional concentration (FIG. 4B) of liver-derived DNA using droplet digital PCR in the plasma of HCC patients.
Figure 4B:
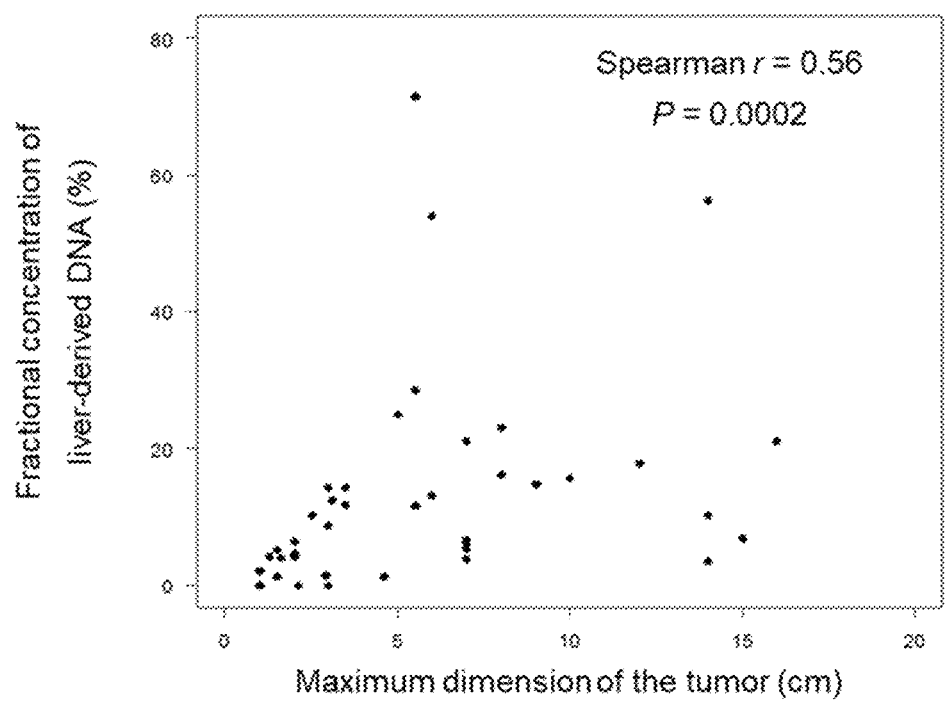

The correlation between the concentrations (absolute and fractional) of liver-derived DNA in plasma and the maximum dimensions of the tumors (determined either by computed tomography scan or measured after tumor resection) in the HCC patients was further analyzed. Interestingly, the maximal dimensions of the tumors showed a stronger positive correlation with the absolute concentrations (R=0.74, P<0.0001, Spearman correlation) than with the fractional concentration (R=0.56, P=0.0002, Spearman correlation) (FIGS. 4A and 4B). The concentration of the liver-derived DNA showed a positive correlation with the maximum dimensions of the tumors in HCC patients indicating that the amount of DNA released from the liver would be reflective of the tumor load.

Figure 5A:
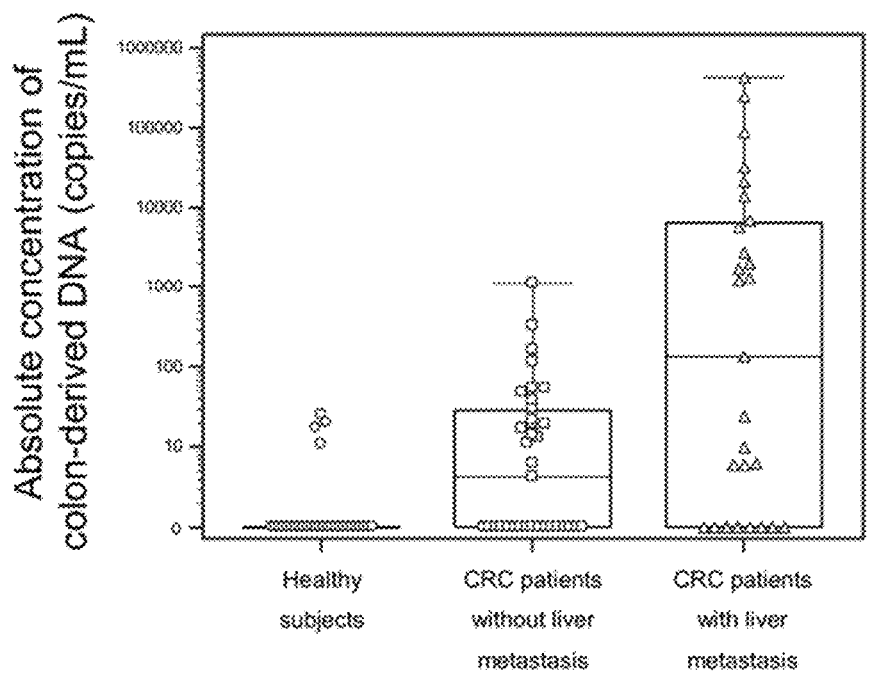
FIGS. 5A-5D show the plasma concentrations of colon- and liver-derived DNA by droplet digital PCR in healthy subjects and CRC patients with and without liver metastases.

Example 5. Analysis of Liver- and Colon-Derived DNA in CRC Patients with and without Liver Metastasis The plasma concentrations of liver-derived and colon-derived DNA were measured in 30 healthy subjects, 35 CRC patients without liver metastasis, and 27 CRC patients with liver metastasis. The median plasma concentrations of colon-derived DNA were 0 copy/mL (IQR: 0-0), 4 copies/mL (IQR: 0-31), and 138 copies/mL (IQR: 0-6850) for the three groups, respectively (FIG. 5A). The concentrations were significantly different between the three groups (P<0.001, Kruskal Wallis test). In the post-hoc analysis, the concentrations of the CRC patients with and without liver metastasis were significantly higher than the healthy subjects (P<0.001 and P=0.042, respectively, Dunn's test). The difference between the CRC patients with and without liver metastasis were not statistically significant (P=0.079, Dunn's test).

Figure 5B:
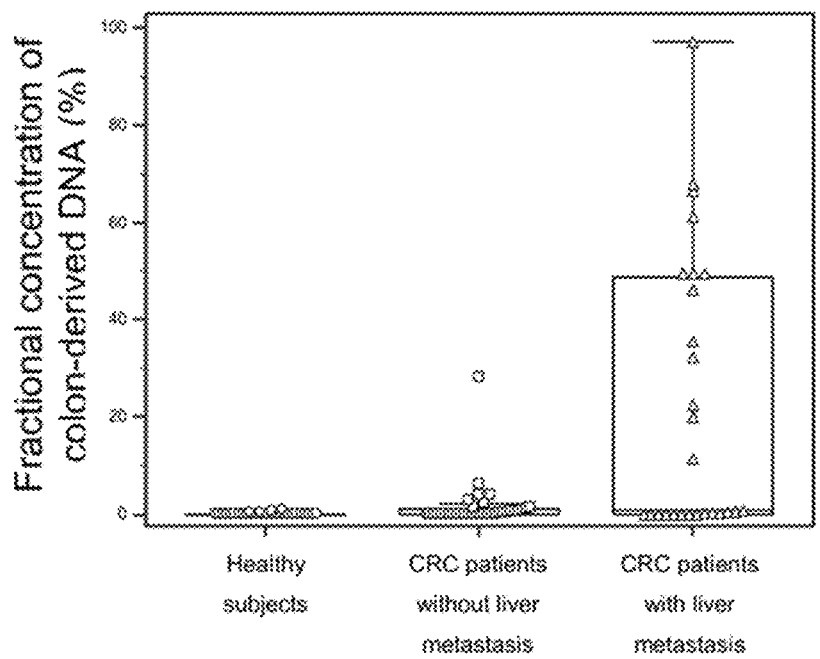

The median fractional concentrations of colon-derived DNA in plasma for the healthy control subjects, CRC patients without liver metastasis, and CRC patients with liver metastasis were 0% (IQR: 0%-0%), 0.09% (IQR: 0%-1.1%), and 0.84% (IQR: 0%-49.5%), respectively (FIG. 5B). The fractional concentrations were significantly different between the three groups (P<0.001, Kruskal Wallis test). In the post-hoc analysis, the concentrations of the CRC patients with and without liver metastasis were significantly higher than the healthy subjects (P<0.001 and P=0.041, respectively, Dunn's test). The difference between the CRC patients with and without liver metastasis was not statistically significant (P=0.084, Dunn's test).

Figure 5C:
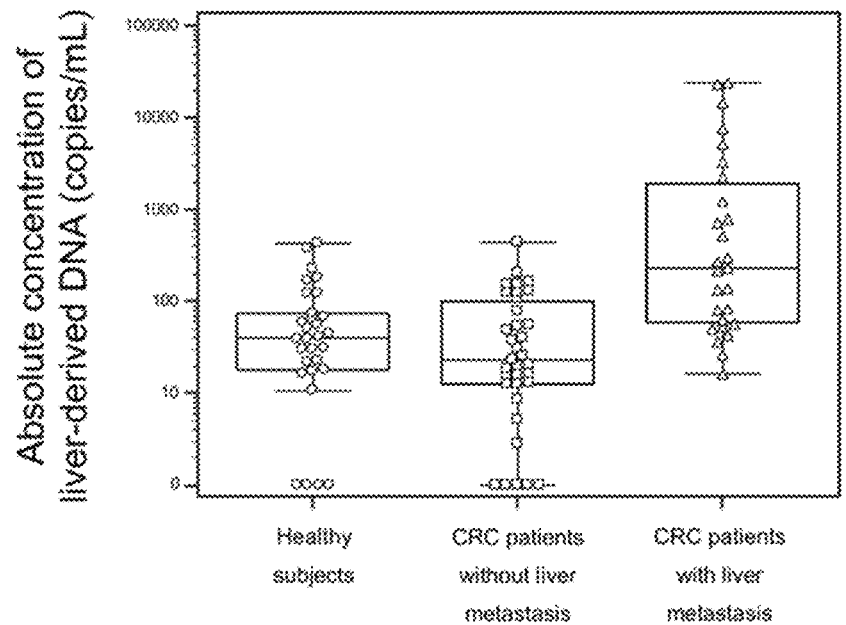

The median concentrations of liver-derived DNA in plasma for the healthy control subjects, CRC patients without liver metastasis, and CRC patients with liver metastasis were 40 copies/mL (IQR: 18-86), 23 copies/mL (IQR: 13-108), and 233 copies/mL (IQR: 56-2290), respectively (FIG. 5C). The fractional concentrations were significantly different between the 3 groups (P<0.001; Kruskal-Wallis test). In the post hoc analysis, the concentrations of the CRC patients with liver metastases were significantly higher than those without liver metastases and the healthy controls (P<0.001 and P<0.001, respectively; Dunn test). Interestingly, there was no significant difference between patients without liver metastases and healthy controls (P=1.0; Dunn test).

Figure 5D:
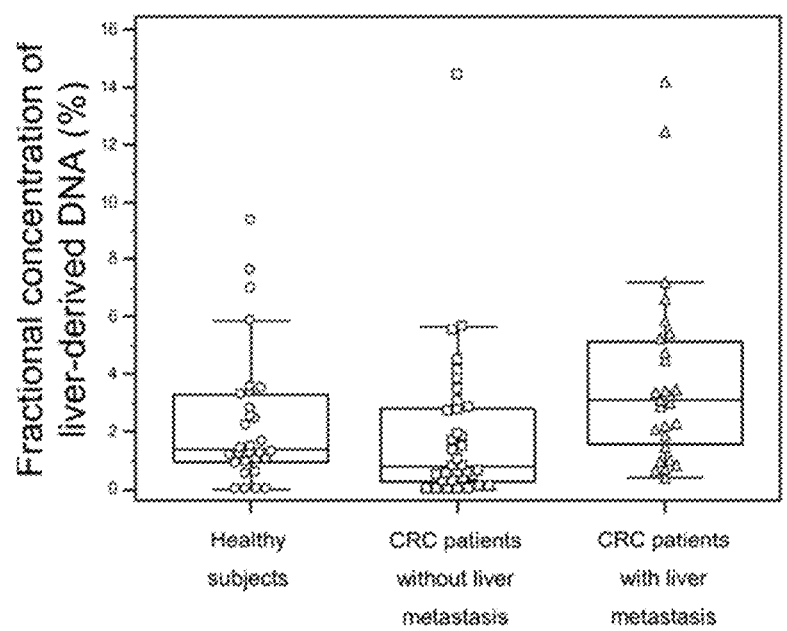

The median fractional concentrations of liver-derived DNA in plasma for the healthy control subjects, CRC patients without liver metastasis, and CRC patients with liver metastasis were 0.8% (IQR: 0.3%-2.8%), 1.4% (IQR: 0.9%-3.3%), and 3.1% (IQR: 1.5%-5.3%), respectively (FIG. 5D). The fractional concentrations were significantly different between the three groups (P<0.001, Kruskal-Wallis test). In the post-hoc analysis, the concentrations of the CRC patients with liver metastasis were significantly higher than those without liver metastasis (P<0.003, Dunn's test). The fractional concentrations of the healthy subjects were not statistically significantly different from the CRC patients with and without liver metastasis (P=0.114 and P=0.717, respectively).

As significant difference was observed between the CRC patients with and without liver metastasis in the absolute and fractional concentrations of liver- and colon-derived DNA in plasma, ROC curve analysis was used to determine which parameter would be most useful for differentiating the two groups. The AUCs for the absolute and fractional concentrations of liver-derived DNA were 0.85 and 0.75 (P=0.01, Delong test), respectively, and AUCs for the absolute and fractional concentrations of colon-derived DNA were 0.69 and 0.69 (P=0.75, Delong test), respectively (FIG. 6).

Figure 6:
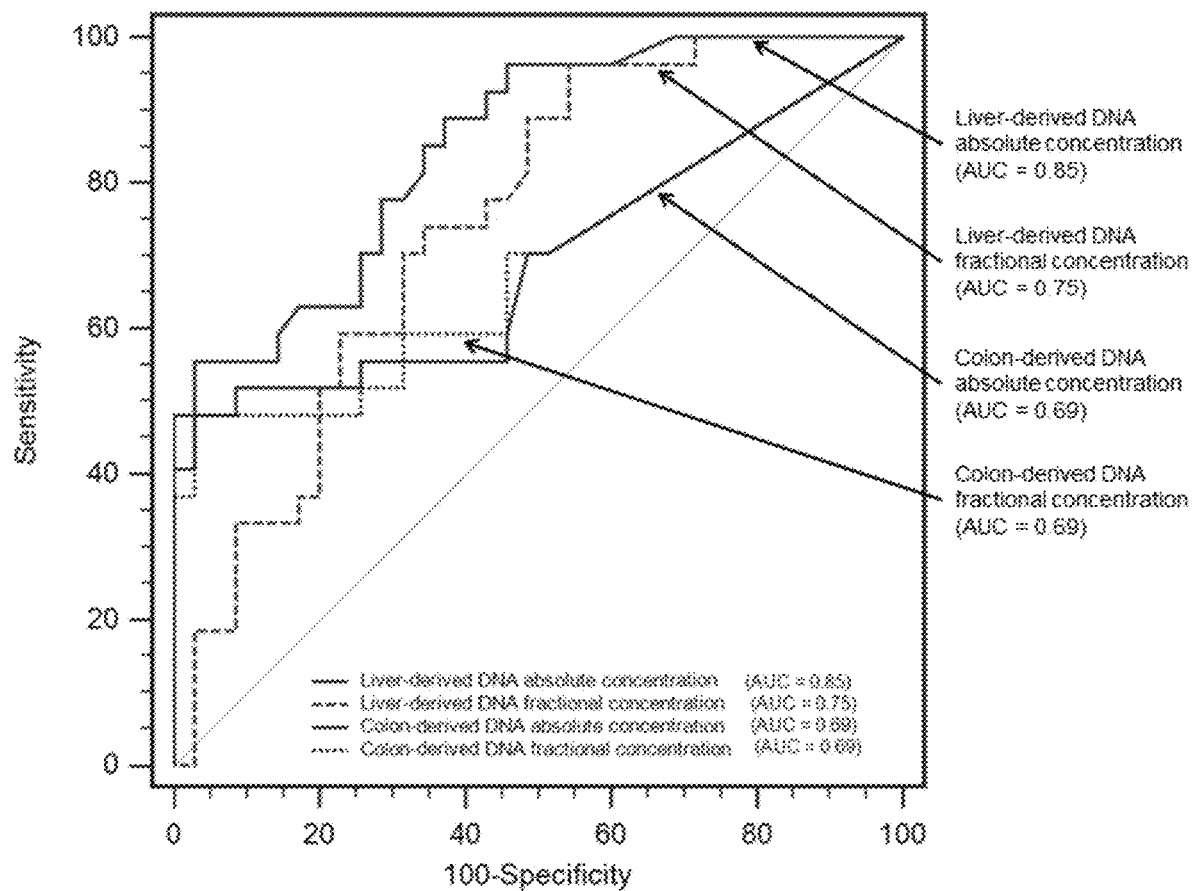
FIG. 6 shows ROC curves for using the absolute and fractional concentrations of liver- and colon-derived DNA to differentiate CRC patients with and without liver metastasis. "AUC" denotes area under curve.

The analysis of the absolute concentrations of liver-derived DNA was better than the fractional concentration in differentiating the CRC patients with and without liver metastasis in the ROC analysis (AUC: 0.85 vs 0.75, P=0.01, FIG. 6). Without being bound by theory, the likely explanation is that in some patients with metastatic CRC to the liver, the absolute concentrations of both the liver- and colon-derived DNA would be increased. In some patients, although the absolute concentration of liver-derived DNA was increased, the fractional concentration of the liver remains unchanged or reduced due to a greater increase in the colon-derived DNA. Similarly, it was also shown that the absolute concentration of liver-derived DNA had a better correlation with tumor size compared with the fractional concentration (R=0.74 vs 0.56, Spearman correlation, FIG. 4).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

What is claimed is:

1. A method of detecting and treating a metastasis in a subject, the method comprising selecting a subject having a metastasis of a cancer with a tissue of origin, and administering a treatment to the subject effective to treat the metastasis, wherein:
   (a) the selecting comprises (i) receiving results of an assay of a first biological sample of the subject measuring an absolute amount of cell-free DNA comprising a target sequence having a first methylation status (ii) identifying the measured absolute amount as being above a reference amount, and (iii) identifying a first non-cancer tissue as a location of the metastasis;
   (b) the first biological sample comprises cell-free DNA molecules from the cancer, the first non-cancer tissue, and one or more second non-cancer tissues;
   (c) the tissue of origin, the first non-cancer tissue, and the one or more second non-cancer tissues are different;
   (d) cell-free DNA molecules from the first non-cancer tissue comprise the first methylation status of the target sequence;
   (e) the first methylation status is distinct from one or more second methylation statuses of the target sequence in cell-free DNA molecules from the cancer and from the one or more second non-cancer tissues;
   (f) the reference amount is an absolute amount of cell-free DNA comprising the target sequence having the first methylation status for one or more subjects without metastasis in the first non-cancer tissue; and
   (g) the treatment is selected from the group consisting of chemotherapy, radiation therapy, surgical removal of tumor tissues, immunotherapy, hormone therapy, and stem cell therapy.

2. The method of claim 1, wherein the first biological sample comprises isolated cell-free DNA molecules comprising the target sequence.

3. The method of claim 2, wherein the assay comprises isolating the cell-free DNA molecules comprising the target sequence in an oil emulsion.

4. The method of claim 1, wherein the assay comprises hybridizing the cell-free DNA molecules comprising the target sequence to a probe, and wherein the probe hybridizes to the target sequence when a methylation site of the target sequence is methylated in the first biological sample, or the probe hybridizes to the target sequence when a methylation site of the target sequence is unmethylated in the first biological sample.

5. The method of claim 1, wherein the assay comprises amplifying the cell-free DNA molecules using a pair of primers, wherein an affinity of hybridization of at least one primer of the pair of primers to the target sequence depends on the first methylation status of the target sequence, and wherein (i) the at least one primer of the pair of primers hybridizes to the target sequence when a methylation site of the target sequence is methylated in the first biological sample, or (ii) the at least one primer of the pair of primers hybridizes to the target sequence when a methylation site of the target sequence is unmethylated in the first biological sample.

6. The method of claim 1, wherein the assay comprises bisulfite conversion of unmethylated cytosine residues in the cell-free DNA molecules to uracil.

7. The method of claim 1, wherein the assay comprises performing methylation-aware sequencing of cell-free DNA molecules from the first biological sample.

8. The method of claim 1, wherein the target sequence comprises at least 5 methylation sites.

9. The method of claim 1, wherein the first methylation status comprises methylation density for individual sites within the target sequence, a distribution of methylated/unmethylated sites over a contiguous region within the target sequence, a pattern or level of methylation for each individual methylation site within the target sequence, or non-CpG methylation.

10. The method of claim 1, wherein the target sequence comprises a higher methylation density in the first non-cancer tissue than in the cancer and in the one or more second non-cancer tissues.

11. The method of claim 10, wherein the target sequence comprises a methylation density in the first non-cancer tissue that is more than 50%, and wherein the target sequence comprises a methylation density in the cancer and in the one or more second non-cancer tissues that is less than 20%.

12. The method of claim 1, wherein the first non-cancer tissue comprises liver tissue, and the target sequence comprises a polynucleotide sequence having at least 60% identity to SEQ ID NO: 1.

13. The method of claim 12, wherein the first non-cancer tissue comprises liver tissue, and wherein the assay comprises amplification using a primer comprising SEQ ID NO: 2, a primer comprising SEQ ID NO: 3, or both, or use of a detectably-labeled probe comprising SEQ ID NO: 4 for detection of the target sequence.

14. The method of claim 13, wherein the amplification further comprises use of a primer comprising SEQ ID NO: 5, a primer comprising SEQ ID NO: 6, or both, or use of a detectably-labeled probe comprising SEQ ID NO: 7 for detection of the target sequence.

15. The method of claim 1, wherein the first non-cancer tissue comprises colon tissue, and the target sequence comprises a polynucleotide sequence having at least 60% identity to SEQ ID NO: 8.

16. The method of claim 15, wherein the first non-cancer tissue comprises colon tissue, and wherein the assay comprises amplification using a primer comprising SEQ ID NO: 9, a primer comprising SEQ ID NO: 10, or both, or use of a detectably-labeled probe comprising SEQ ID NO: 11 for detection of the target sequence.

17. The method of claim 16, wherein the amplification further comprises use of a primer comprising SEQ ID NO: 12, a primer comprising SEQ ID NO: 13, or both, or use of a detectably-labeled probe comprising SEQ ID NO: 14 for detection of the target sequence.

18. The method of claim 1, wherein the cancer is selected from the group consisting of: bladder cancer, bone cancer, brain tumor, breast cancer, carcinoma of cervix, colorectal cancer, esophageal cancer, gastrointestinal cancer, hematopoietic malignancy, head and neck squamous cell carcinoma, leukemia, liver cancer, lung cancer, lymphoma, myeloma, nasal cancer, nasopharyngeal cancer, oral cancer, oropharyngeal cancer, ovarian cancer, prostate cancer, sarcoma, stomach cancer, melanoma, and thyroid cancer.

19. The method of claim 1, further comprising determining a classification of the cancer in the first non-cancer tissue, which comprises receiving results of an assay assessing cell-free nucleic acid molecules from a second biological sample from the subject, and wherein the assessing comprises determining methylation profile, copy number variations, single polymorphism (SNP) profile, or fragmentation pattern of the cell-free nucleic acid molecules from the second biological sample.

20. The method of claim 1, wherein the treatment is selected from the group consisting of: chemotherapy, radiation therapy, and surgical removal of tumor tissues.

\* \* \* \* \*

SEQUENCE LISTING

<160> NUMBER OF SEQ ID NOS: 18

<210> SEQ ID NO 1
<211> LENGTH: 61
<212> TYPE: DNA
<213> ORGANISM: Homo sapiens

<400> SEQUENCE: 1
cggccgactt acctgtactt gccgccgtcc cggctcacct ggcggtgccc gaggagtagt     60
c                                                                    61

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttatttgtt cggtcgattt atttgta                                        27

```
<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aacgactact cctcgaacac cg                                              22

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ttgtcgtcgt ttcggtt                                                    17

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtatattta tttgtttggt tgatttattt gta                                  33

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccaacaacta ctcctcaaac acca                                            24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tttgttgttg ttttggttta                                                 20

<210> SEQ ID NO 8
<211> LENGTH: 60
<212> TYPE: DNA
<213> ORGANISM: Homo sapiens

<400> SEQUENCE: 8
cgcaacctgc tcccgagtga gaacaaaggc cggcgcagag cgagaacctg attggtgccc     60

<210> SEQ ID NO 9
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cgtaatttgt tttcgagtga gaataa                                          26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaaaccgaa caccaatcaa attc                                            24

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
tcggcgtaga gcga                                                       14

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtttgtaatt tgttttgag tgagaataa                                        29

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaaaaccaaa caccaatcaa attc                                            24

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
aggttggtgt agagtga                                                    17

<210> SEQ ID NO 15
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 15
ttgtcgtcgt ttcggtt                                                    17

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tttgttgttg ttttggttta                                                 20

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tcggcgtaga gcga                                                       14

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
aggttggtgt agagtga                                                    17
```